(12) United States Patent
Soller et al.

(10) Patent No.: US 7,245,373 B2
(45) Date of Patent: Jul. 17, 2007

(54) SPECTROMETER SYSTEM FOR OPTICAL REFLECTANCE MEASUREMENTS

(75) Inventors: Babs R. Soller, Northboro, MA (US); Patrick G. Phillipps, Lincoln, MA (US); Michael S. Parker, Uxbridge, MA (US)

(73) Assignees: University of Massachusetts, Boston, MA (US); NIRStat LLC, Chatham, MA (US)

( * ) Notice: Subject to any disclaimer, the term of this patent is extended or adjusted under 35 U.S.C. 154(b) by 146 days.

(21) Appl. No.: 11/113,347

(22) Filed: Apr. 25, 2005

(65) Prior Publication Data

US 2005/0259254 A1   Nov. 24, 2005

Related U.S. Application Data

(60) Provisional application No. 60/565,557, filed on Apr. 26, 2004, provisional application No. 60/565,655, filed on Apr. 26, 2004.

(51) Int. Cl.
*G01J 3/10* (2006.01)
*G01J 3/28* (2006.01)

(52) U.S. Cl. .................. 356/325; 356/326; 315/307

(58) Field of Classification Search ........... 356/323, 356/325, 326, 328
See application file for complete search history.

(56) References Cited

U.S. PATENT DOCUMENTS

| | | | |
|---|---|---|---|
| 4,030,829 A | * | 6/1977 | Hooper ................. 356/325 |
| 4,464,051 A | | 8/1984 | Talmadge et al. |
| 5,042,948 A | * | 8/1991 | Fletcher ................. 356/328 |
| 5,184,193 A | | 2/1993 | LeFebre |
| 5,652,654 A | | 7/1997 | Asimopoulos |
| 6,002,477 A | | 12/1999 | Hammer |

* cited by examiner

*Primary Examiner*—F. L. Evans
(74) *Attorney, Agent, or Firm*—Fish & Richardson P.C.

(57) ABSTRACT

A spectrometer system includes a thermal light source for illuminating a sample, where the thermal light source includes a filament that emits light when heated. The system additionally includes a spectrograph for measuring a light spectrum from the sample and an electrical circuit for supplying electrical current to the filament to heat the filament and for controlling a resistance of the filament. The electrical circuit includes a power supply that supplies current to the filament, first electrical components that sense a current through the filament, second electrical components that sense a voltage drop across the filament, third electrical components that compare a ratio of the sensed voltage drop and the sensed current with a predetermined value, and fourth electrical components that control the current through the filament or the voltage drop across the filament to cause the ratio to equal substantially the predetermined value.

24 Claims, 13 Drawing Sheets

SPECTROMETER SYSTEM FOR OPTICAL REFLECTANCE MEASUREMENTS

CLAIM OF PRIORITY

This application claims priority under 35 USC § 119(e) to U.S. patent application Ser. No. 60/565,557, filed on Apr. 26, 2004, and to U.S. patent application Ser. No. 60/565,655, filed on Apr. 26, 2004, the entire contents of both applications being hereby incorporated by reference for all purposes.

STATEMENT AS TO FEDERALLY SPONSORED RESEARCH

Funding for the work described herein was provided by the US Army Medical Research Command, Contract Number DAMD17-03-1-0005, and by the National Space Biomedical Research Institute, Grant Number SMS00205, funded under NASA Cooperative Agreement NCC9-58. The Federal Government may have certain rights in the invention.

TECHNICAL FIELD

This invention relates to spectrometer systems and methods, and more particularly to spectrometer systems for reflectance measurements.

BACKGROUND

Optical spectroscopy can be used to determine the concentration of chemical species in gaseous, liquid, and solid solutions. The amount of light absorbed by a particular chemical species is often linearly related to its concentration through Beer's Law, $A = \in lc$, where A is termed absorbance, $\in$ is a constant specific to the chemical, 1 is the path length of light, and c is the concentration. $A = \log(I_0/I)$, where $I_0$ is the intensity of incident light, and I is the intensity of light after it has passed through a solution containing the chemical to be measured.

For nontransparent materials, including complex materials such as powders, tablets, natural materials (soil, agricultural products), blood, skin, and muscle, optical information can be collected via diffuse reflectance spectroscopy. In this setting, $A = (I_{100}/I_R)$, where $I_{100}$ is the light reflected from a 100% diffuse reflectance standard, the equivalent of the incident light, and $I_R$ is light reflected from the material under study. The concentration of a chemical component in one of these complex materials is related to A, though often not linearly. More sophisticated mathematical techniques, such as, for example, partial least squares regression and other multivariate calibration methods are used to determine a relationship between concentration and absorbance. Once these calibration models are derived, they can be used to determine chemical composition by measuring absorbance in the transmittance or reflectance mode.

In the laboratory, it is relatively straightforward to measure the absorbance A. One method uses a temperature controlled dual beam spectrograph. The sample solution is placed in one chamber, and the amount of light transmitted through the sample is measured. The solvent alone is placed in the second chamber where the incident light is measured. The ratio is determined electronically and the absorbance reported.

Laboratory spectrographs are generally large, expensive, and not portable. Recently, smaller spectrographs have been introduced that allow absorbance measurements to be performed in the "field," meaning that the spectrometer equipment can be brought to the sample, rather than requiring that the sample be brought to the lab.

Spectroscopic measurements are now commonly made of agricultural products, in the ocean and in forests, on manufacturing production lines, and on the human body. Most of these measurements are made in the reflectance mode in which a fiber optic based sensor directs light to the sample and measures light reflected back from the sample. Field measurements are often made in an ongoing, continuous manner, to observe temporal changes of a quantity measured spectrographically. Sometimes these measurements are made in a "hostile" environment, where it is difficult to make electrical measurements because these sensors experience interference (e.g., in an MRI machine) or degradation (e.g., due to a smoke stack or waste water).

Usually these measurements are made by first collecting light from the 100% reflectance standard, storing that number, then attaching the sensor to the sample and collecting a series of spectra. The initial reference measurement of the 100% reflectance standard is used to calibrate absorbance from all subsequent sample spectra. This process, unfortunately, can introduce significant error, especially when the target absorbance changes are small and present in a complex, interfering chemical mixture, such as those studied in the field. Over time there can be changes in the lamp output and the detector sensitivity, which alter the intensity and spectral temperature of light impinging on the sample. If these changes are not detected and corrected in real time in the absorbance calculation, the measured value of A will be erroneous, and an accurate concentration of the measured quantity cannot be made.

SUMMARY

The invention features new spectrometer systems used for analyzing samples by shining light them, collecting light reflected by the sample, and analyzing the reflected light in a spectrometer. Because the spectrum of light shined on the sample is controlled to be very stable, the spectrometer measurements are highly stable. Moreover, as the system continually monitors the sample over a period of time the system can be continuously calibrated to minimize errors that accumulate over time due to temporal drift in properties of the lamp, the spectrometer, and/or other elements of the system.

In a first general aspect, a spectrometer system includes a thermal light source for illuminating a sample, where the thermal light source includes a filament that emits light when heated. The system additionally includes a spectrograph for measuring a light spectrum from the sample and an electrical circuit for supplying electrical current to the filament to heat the filament and for controlling a resistance of the filament. The electrical circuit includes a power supply that supplies current to the filament, first electrical components that sense a current through the filament, second electrical components that sense a voltage drop across the filament, third electrical components that compare a ratio of the sensed voltage drop and the sensed current with a predetermined value, and fourth electrical components that control the current through the filament or the voltage drop across the filament to cause the ratio to equal substantially the predetermined value.

Implementations can include one or more of the following features. For example, the first electrical components can include a sense resistor, where a voltage across the sense resistor is proportional to the current through the filament. The second electrical components can include a differential amplifier that generates a signal proportional to a voltage drop across the filament. The third electrical components can include a differential amplifier that compares a signal indicative of a current through the filament with a signal indicative of a voltage drop across the filament. The system can further include a voltage divider that multiples a ratio between the signal indicative of the current through the filament and the signal indicative of the voltage drop across the filament by a conversion factor.

The fourth electrical components can include a transistor adapted for driving the filament with a current to ensure a substantially constant filament temperature. The system can further include fifth electrical components that gradually ramp up the current supplied to the filament when the power to the filament is turned on. The fifth electrical components can include a low pass filter. The system can further include sixth electrical components that limit the current supplied to the filament below a maximum value.

In another general aspect, the invention also includes methods of controlling a spectrum of light emitted from a heated filament by supplying electrical current from a power supply to heat the filament, sensing a current flowing through the filament, sensing a voltage drop across the filament, comparing a ratio of the sensed voltage drop and the sensed current with a predetermined value, and controlling the current or the voltage drop to cause the ratio to equal the predetermined value.

Implementations can include one or more of the following features. For example, the methods can further include compensating for a temperature-dependent change in a resistance of electrical connectors that supply current to the filament by introducing an additional temperature-dependent change in an electrical connection between the power supply and the filament. The filament can be driven with a current controlled to ensure a substantially constant filament temperature. The current supplied to the filament can be gradually ramped up when the power to the filament is turned on. The methods can further include shining the light on a sample, collecting light scattered from the sample, and analyzing the collected light in a spectrograph to measure properties of the sample.

In a further general aspect, the invention features spectrometer systems that include a light source, a spectrograph, an first optical beam path for guiding light from the light source to a sample, a second optical beam path for guiding light from the light source to the spectrograph, a third optical beam path for guiding light reflected from the sample to the spectrograph, a shutter for blocking and unblocking the light in the first beam path from the sample and for blocking and unblocking light in the second beam path from the spectrograph, and a processor adapted for analyzing light spectra from light guided into the spectrograph and adapted for correcting the spectra for a dark current in the system based on spectra recorded when both the first and second optical beam paths are blocked and adapted for correcting the spectra for temporal changes in the spectrum of the light source based on a plurality of spectra recorded at different times when light is guided into the spectrograph along the second beam path.

Implementations can include one or more of the following features. For example, the first optical beam path can included a first optical fiber and the second optical beam path can include a second optical fiber that is optically shielded from the first optical fiber.

The system can further include a memory adapted for storing an initial lamp spectrum and a later lamp spectrum recorded from light guided to the spectrograph through the second beam path, where the later lamp spectrum is recorded at a time later than the initial lamp spectrum, and adapted for storing an initial reference spectrum recorded from light guided through the first optical beam path to a reference sample, scattered by the reference sample having a known reflectance spectrum, and guided to the spectrograph from the sample through the third optical beam path. The processor can be further adapted for correcting a spectrum of light that has been guided to a test sample from the light source and scattered from the sample to the spectrograph, where the correction is based on the initial lamp spectrum, the later lamp spectrum, and the initial reference spectrum.

The light source can include a filament that emits light when heated, and the system can further include an electrical circuit for supplying electrical current to the filament to heat the filament and for controlling a resistance of the filament, where the electrical circuit includes a power supply that supplies current to the filament, first electrical components that sense a current through the filament, second electrical components that sense a voltage drop across the filament, third electrical components that compare a ratio of the sensed voltage drop and the sensed current with a predetermined value, and fourth electrical components that control the current through the filament or the voltage drop across the filament to cause the ratio to equal substantially the predetermined value. The fourth electrical components can be adapted for driving the filament with a current controlled to ensure a substantially constant filament temperature.

In another general aspect, the invention includes methods for correcting a spectrum measured by a spectrometer system having a spectrograph and a light source for illuminating a sample with light output from the light source. These methods include recording a reference spectrum, $Ro(\lambda)$, from a reference sample having a known reflectivity spectrum when light from the light source is shined on the reference sample, recording an initial lamp spectrum, $Lo(\lambda)$, of the light output from the light source at an initial time when light from the light source is shined into the spectrograph, recording a subsequent lamp spectrum, $Lt(\lambda)$, of the light output from the light source at a time later than the initial time when light from the light source is shined into the spectrograph, recording a spectrum from a test sample, $S(\lambda)$, and correcting the spectrum from the test sample using data from the reference spectrum, the initial lamp spectrum, and the subsequent lamp spectrum.

Implementations can include one or more of the following features. For example, the reference sample can reflect approximately 100% of light directed at the reference sample over a predetermined wavelength range. Correcting the spectrum can include multiplying the spectrum, $S(\lambda)$, by $Ro(\lambda)*(Lt(\lambda)/Lo(\lambda))$. Light from the light source can be directed toward the reference sample, the test sample, or the spectrograph depending on a position of a shutter that is adapted to selectively block light from reaching the reference sample, the test sample, or the test sample. The position of the shutter can be changed by rotating the shutter about an axis.

In a further general aspect, the invention features spectrometer systems that include a light source, a spectrograph, an first optical beam path for guiding light from the light source to a probe head in contact with a sample, where the probe head includes an illumination light port for shining light from the light source onto the sample and a detection light port for collecting light reflected by the sample. A second optical beam path guides light reflected by the sample from the probe head to the spectrograph, and an opaque light shield is attached to the probe head and prevents ambient light from being reflected by the sample into the detection light port.

Implementations can include one or more of the following features. For example, the light shield can include openings through which the detection and illumination light ports fit. The light shield can be adapted to be strapped, tied, or adhered against the sample. The system can further include a cable for guiding light between the light source and the probe head, and a clip for holding a portion of the cable close to probe head in a fixed position relative to the probe head.

The invention provides several advantages. For example, the stability of the lamp filament resistance creates a highly-stable output spectrum from the lamp, such that spectra measured over a period of time are affected very little by changes in the output spectrum of the lamp. Also, the new systems provide real-time updating of the diffuse reflectance standard used to mathematically calculate absorbance. This allows accurate measurements of sample absorbance by correcting for any fluctuation in dark current of the spectrograph or in the lamp output. This compensation allows one to use less expensive, non-cooled detectors in the spectrograph. The new systems also monitor lamp intensity by using transmittance through an attenuating medium, and by using a separate off-axis collection fiber. These features add to the compact and robust nature of the new system.

The new systems include a highly compact optical bench, a novel probe and a miniature spectrograph, that together provide a portable, highly stable spectroscopic system for data collection outside the laboratory that uses minimal energy, has immediate start-up for emergency situations, and provides stable, precise, and accurate measurements for short and long term monitoring.

Unless otherwise defined, all technical and scientific terms used herein have the same meaning as commonly understood by one of ordinary skill in the art to which this invention belongs. Although methods and materials similar or equivalent to those described herein can be used in the practice or testing of the present invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

Other features and advantages of the invention will be apparent from the following detailed description, and from the claims.

DESCRIPTION OF DRAWINGS

Like reference symbols in the various drawings indicate like elements.

DETAILED DESCRIPTION

The new spectrometer systems for making reflectance measurements generally include a light source (e.g., having a near infrared spectrum between 650-1000 nm) for illuminating a sample and a spectrograph for analyzing light reflected from the sample. A spectrometer system can include separate fiber optic cables for delivering light from the lamp to the sample, for delivering reflected light from the sample to the spectrograph, and for delivering light directly from the lamp to the spectrograph. The lamp is powered by an electrical feedback circuit to ensure stable operation of the lamp. A movable shutter located between the light source and the fiber optic cables that deliver light to the sample and to the spectrograph can determine which one of the cables is illuminated by the light source. When a cable leading to the sample is illuminated, reflectance spectra from the sample can be recorded. When a cable leading to the spectrograph is illuminated, spectra of the light source can be recorded and used to calibrate the sample spectra. By moving the shutter between several positions, the sample spectra can be continuously calibrated over a period of time.

Overall System

Figure 1:
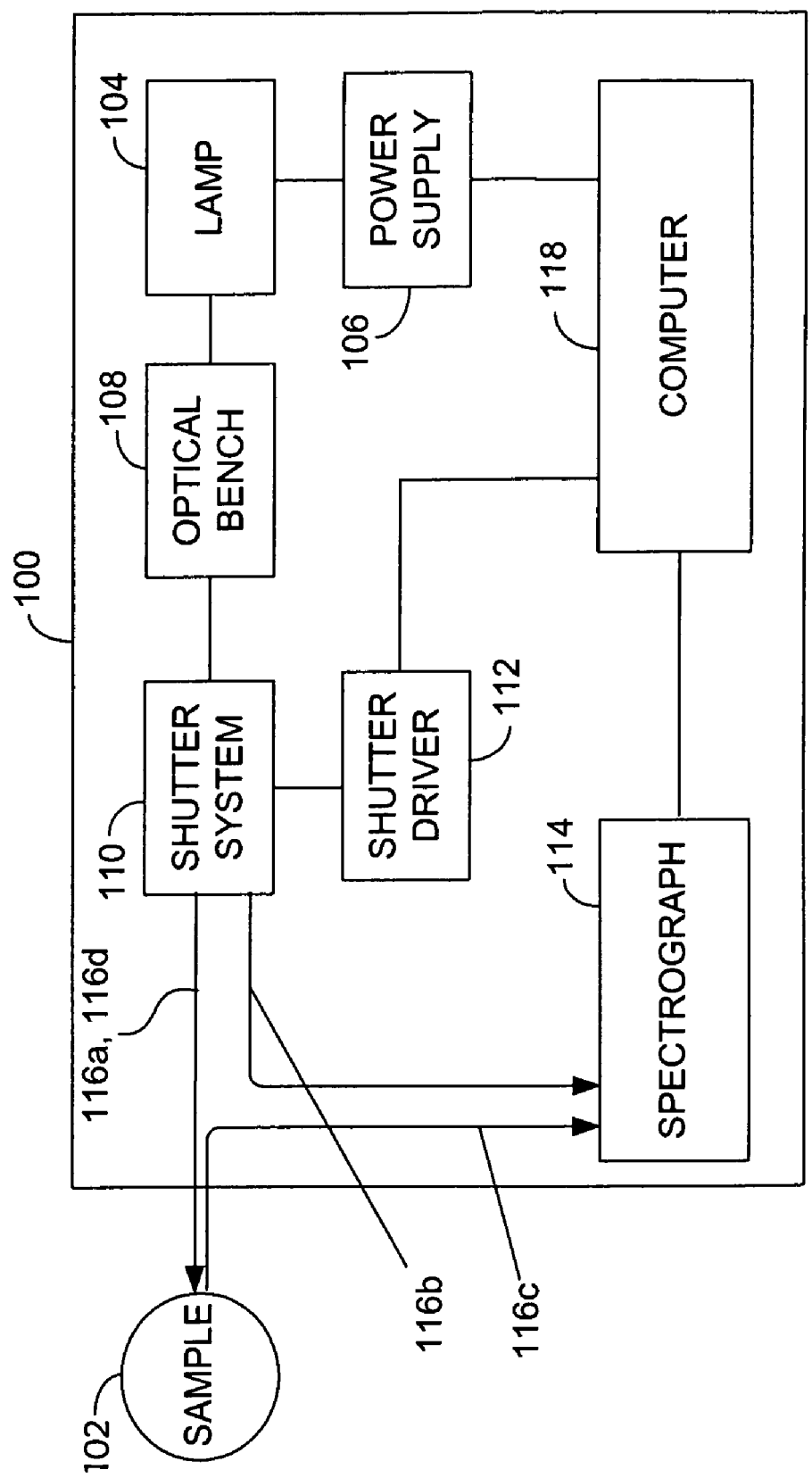
FIG. 1 is a schematic diagram of a spectrometer system described herein.

As shown in FIG. 1, a portable, fiber-optic-based spectroscopic system 100 for collection of reflectance spectra from a sample 102 located remotely from the system includes a lamp 104, a power supply 106 for the lamp 104, an optical bench 108, a shutter system 110, a driver for the shutter system 112, a spectrograph 114, a fiber optic cable 116, and a computer 118. Light from the lamp is manipulated by optics within the optical bench 106 and can be controlled by a shutter system 110 that is driven by a shutter driver 112. Light can be passed by the shutter system 110 into a fiber optic cable 116a or 116d and guided to the sample 102 to illuminate the sample or can be passed by the shutter system 110 into a second portion of the fiber optic cable 116b and guided to the spectrograph 114.

When light is guided to the sample in the fiber optic cable 116a or 116d, light reflected from the sample 102 is guided by a third portion of the fiber optic cable 116c from the sample 102 to the spectrograph 114. Reflected light from the sample 102 is analyzed by the spectrograph 114 to gather information about the sample 102. The analysis can be calibrated by spectral analysis of light guided directly to the spectrograph 114 from the optical bench 108 in optical fiber 116b and by the signal from the spectrograph 114 when no light is fed into the spectrograph 114.

The system 100 further includes an on-board computer 118 for controlling the shutter driver 112, the spectrograph 114, and for processing, storing, and displaying data from the spectrograph.

The spectrograph 114 can be any off-the-shelf portable spectrograph that can be operated by computer control. For example, an Ocean Optics USB2000 spectrograph with a grating optimized for performance in the wavelength range of 500 nm-1000 nm. The spectrograph detector can be a 2048 element shallow-well linear CCD-array. The spectrograph can be equipped with a 200 micron wide slit to increase resolution, a collection lens to increase light collection efficiency at the detector, and a long pass filter to block light with a wavelength less than 475 nm from reaching the detector. The USB2000 spectrograph interfaces with the computer 118, e.g., through either a USB or RS232 port.

Figure 2:
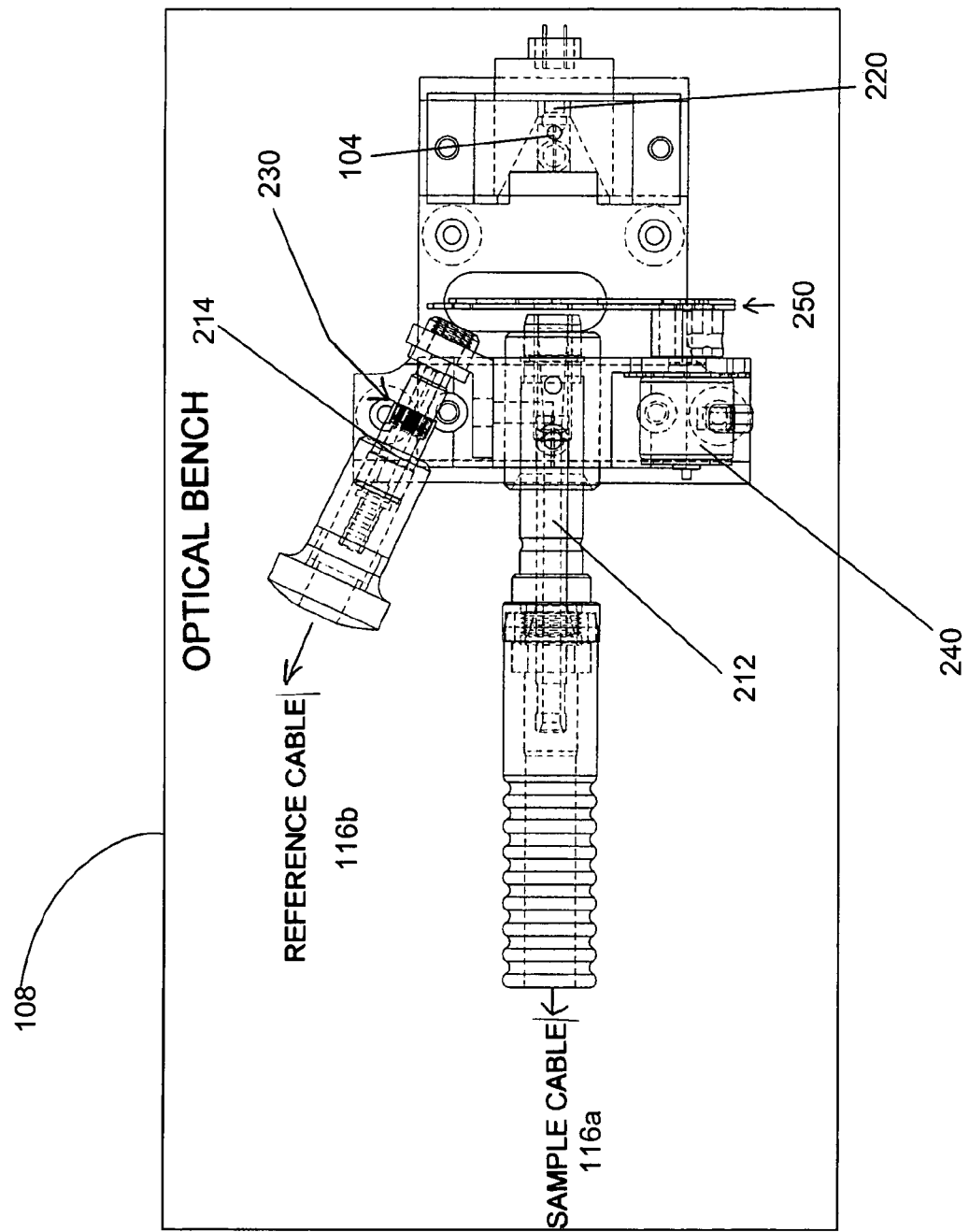
FIG. 2 is a top schematic view of an optical bench and selected components of the spectrometer system of FIG. 1.

As shown in FIG. 2, the optical bench 108 holds several primary optical components. An illumination lamp 104 provides light to illuminate a sample. A first optical connector 212 couples the light to a fiber-optic cable 116a for carrying light to illuminate the object 102. A second optical connector 214 couples light either to a second fiber-optic cable 116b for monitoring the lamp spectrum or to a second fiber-optic cable 116d that carries light to illuminate the object 102. A shutter 250 can select whether of the fiber-optic cable 116a, the fiber optic cable 116b or 116d, or none of the cables is illuminated. The optical bench 108 is used to set up and maintain proper alignment of the above-mentioned optical components to enhance the accuracy and reproducibility of the system 100 as a reflectance spectroscopy measurement system. The optical bench 108 can be fabricated from aluminum because aluminum can be easily machined to close tolerances and has high thermal conductivity to promote heat dissipation and minimize thermal stress and distortion on the components of the system 100.

The lamp 104 is a white light source (e.g., a tungsten-halogen 9 W bulb, Welch-Allyn 8106-001) that is driven by a specially designed power supply 106 to allow for fast ramp-up and stable operation of the lamp. The lamp 104 can be a continuous wave ("cw") light source or a pulsed light source. The lamp 104 is housed within its own machined reflector, so that it is relatively easy to replace when necessary, and its optical alignment is assured through the design of the optical bench. The lamp rests against mechanical stops that ensure that it is accurately located with respect to the fiber optic cables 116a, 116b, and 116d. Light from the lamp 104 is focused down a center axis of the optical bench 108 by a rear reflector 220 (e.g., an ellipsoidal reflector).

Figure 3A:
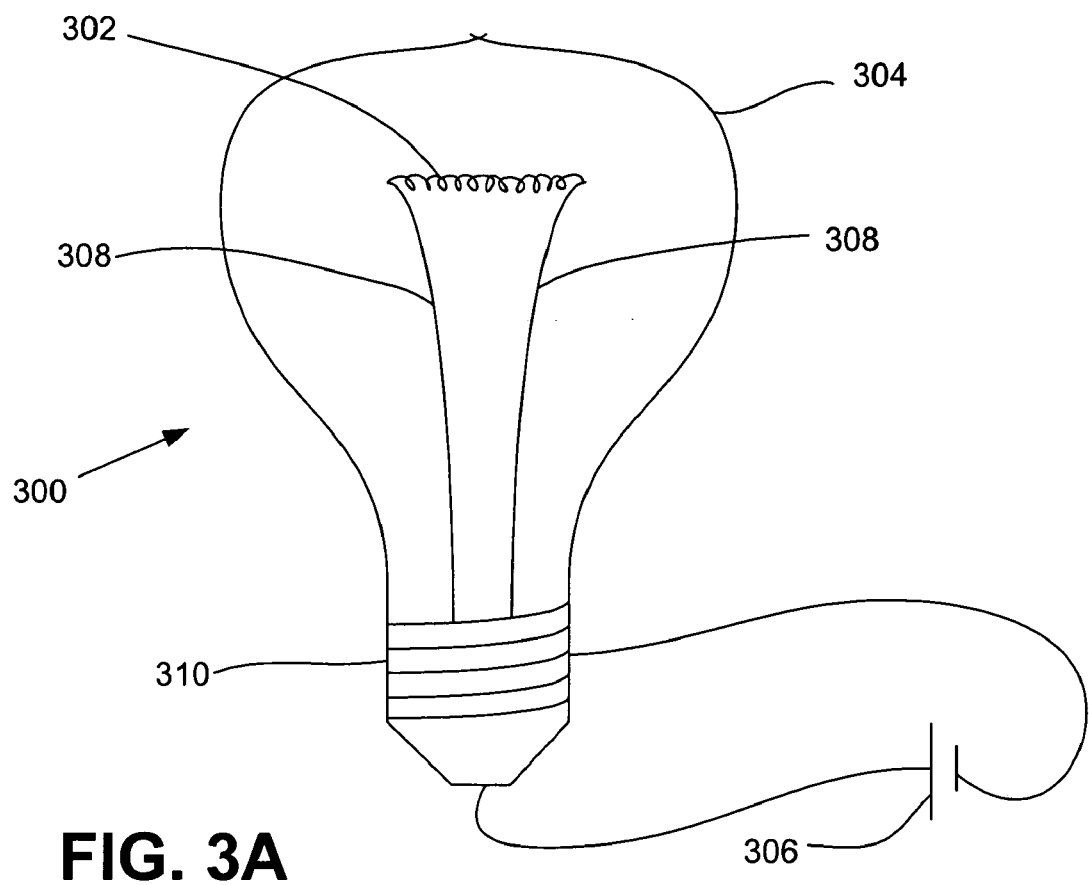
FIG. 3A is a schematic diagram of an incandescent lamp.

The general lamp configuration is illustrated schematically in FIG. 3A, which shows the general features of an incandescent light source 300 that includes an electrically resistive filament 302 within a transparent bulb 304. The filament 302 generally is made of tungsten. The bulb 304 can be made of glass, quartz, or other materials and can be evacuated or can be filled with a halogen gas, an inert gas, or a mixture of gases. Electrical current is supplied from a power supply 306 to the filament 302 through electrically conductive lead wires 308 that are electrically connected to the base 310 of the light source. The electrical current causes the filament to radiate as a black body. The power supply 306 can supply direct current (DC) or alternating current (AC). A version of the light source 300 can be used as the lamp 104 in the system 100, and a stabilized version of the power supply 306 can be used as the power supply 106 in the system 100.

Lamp Power Supply and Stabilization Circuits

The total electromagnetic energy emitted by a black body, according to Stefan's law, is equal to $$I_{T=\sigma eT^4}, \tag{1}$$

where $I_T$ is the intensity of the emitted energy, $\sigma$ is the Stefan-Boltzmann constant, e is the emissivity of the black body material, and T is the temperature of the black body in Kelvin. The spectral distribution of the energy emitted from the black body is equal to $$\rho_T(\lambda) = 8\pi hc/\lambda^5(e^{hc/k\lambda T}-1), \tag{2}$$

where $\rho_T(\lambda)$ is the intensity as a function of wavelength, $\lambda$ is the wavelength, h is Planck's constant, c is the velocity of light, k is Boltzmann's constant, and T is temperature of the source. Thus, the total light output from a filament lamp is proportional to the fourth power of the temperature, and the spectral distribution is similarly a strong function of the filament temperature.

When power is first applied to a filament lamp 300, the filament 302 heats up until the power emitted by the filament (both radiant power and conducted power) equals the power applied to the filament (i.e., the voltage across the filament multiplied by the current through it). The resistance, R, of the filament is a function of the filament's temperature, T, $$R=f(T) \tag{3}$$

Nearly all incandescent lamp filaments are made of tungsten, which has a positive coefficient of resistance versus temperature. Thus, as the filament heats up, its resistance increases and its power dissipation declines according to the relation $P=V^2/R$, where P is the dissipated power, V is the voltage drop across the filament, and R is the resistance of the filament. If a constant voltage is applied across the lamp, the filament 302 reaches initial equilibrium within seconds and provides nominally stable light output. However, as the filament support wires 308 heat up they conduct less heat away from the filament 302, the filament becomes hotter, and its light output increases. Similarly, as the lamp base 310 and mount heat up, the filament 302 continues to increase in temperature, and its light output rises. Although these effects increase the filament temperature only slightly, the strong dependence of light output on temperature means that small increases in filament temperature translate into relatively large increases in light output. Because of the long time required for a lamp and its support structure to reach thermal equilibrium, an hour can be required to reach stable light output. If the temperature of the environment changes, the lamp's output will also vary with the temperature of the environment.

As electrical power is initially supplied and dissipated in filament 302, the temperature, T, of the filament rises, causing the filament to emit light having an intensity and spectral distribution given by equations (1) and (2). To achieve a stable light intensity and spectral distribution from the light source 300, the temperature of the filament is stabilized. By measuring the electrical properties of the filament 302, a lamp driver circuit can indirectly measure the filament temperature. Because the resistance of the filament 302 is a direct function of the filament temperature, a constant filament temperature can be maintained by driving the filament at a constant resistance.

The light source 300 can be an incandescent lamp, for example, a Welch-Allyn 7106-0003 lamp, having a desired operating filament resistance of 5 Ohms when supplied with 5 Volts and 1 Amp of current. Other incandescent filament lamps can also be used.

Figure 4:
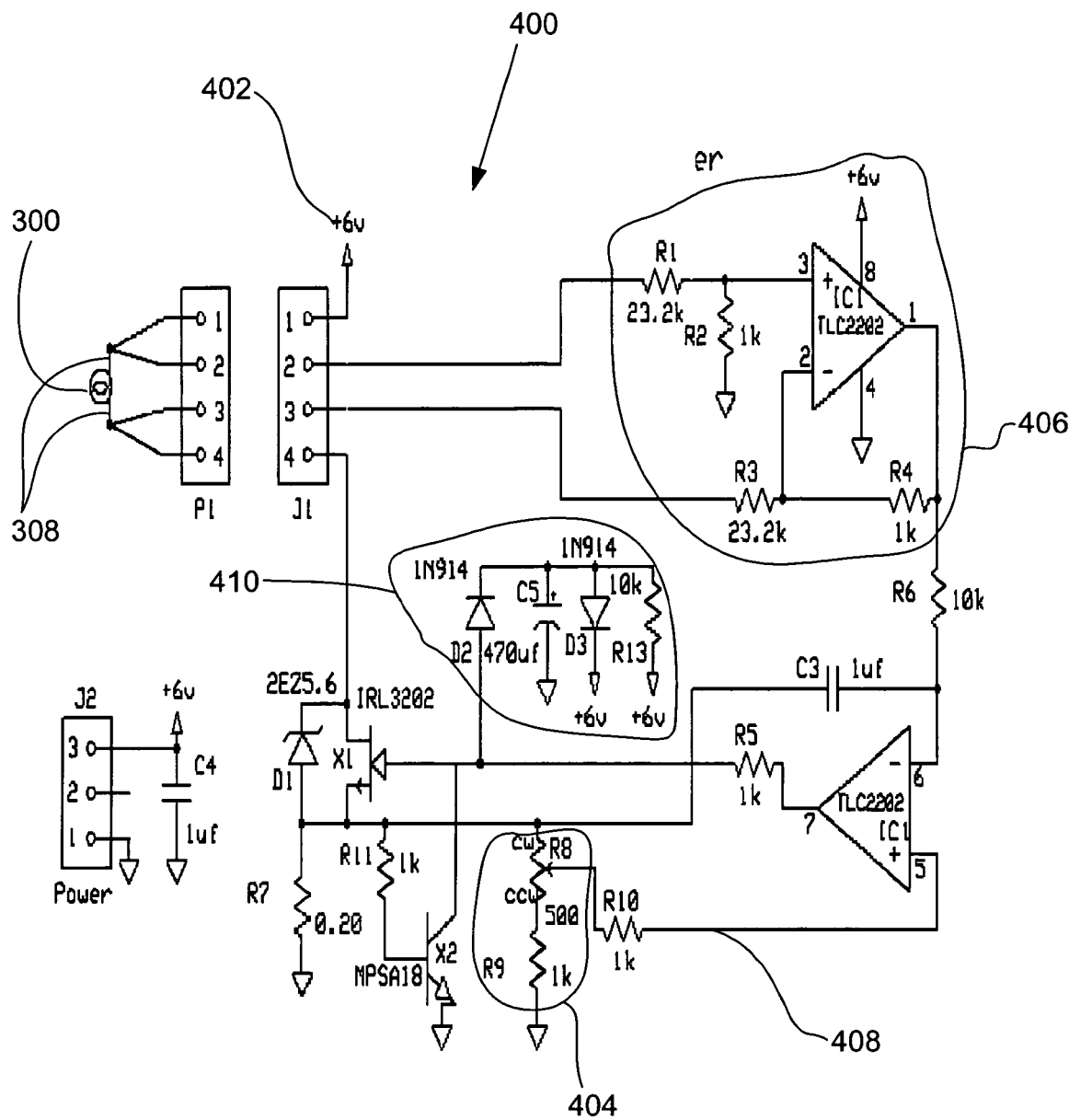
FIG. 4 is a circuit diagram of an electrical circuit for supplying electrical power to a resistive element.

A diagram of a useful circuit 400 for powering a lamp to achieve a stable lamp spectrum is shown in FIG. 4. A relatively unstabilized power supply 402 (e.g., a 6 volt power supply) supplies electrical energy to lead wires 308 of the light source 300. Power is supplied to the lead wires 308, and the voltage across the filament 302 of the lamp is measured. Filament resistance can be computed, for example, by sensing the voltage drop across the filament 302 and the current flowing through the filament and dividing the voltage by the current. To minimize cost and circuit complexity, the circuit drives the lamp voltage to an operating point that is a fixed multiple of the lamp current. This drives the lamp to the desired filament resistance (e.g., 5Ω) without the complexity of actually dividing the lamp voltage by the lamp current to compute filament resistance. Thus, the general, relatively unstabilized power supply 402 is stabilized to create a stable power supply 106 that can be used to drive the light source 104 in a manner to provide a stable output spectrum.

The lamp filament current, $I_L$, is sensed by a sense resistor, e.g., a 0.25 Ω resistor, R7. The voltage drop across R7 is measured and translates the lamp current into a voltage at a conversion factor of 250 mV/amp. A voltage divider 404 that includes resistors R8 and R9 can reduce the conversion factor, for example to 215 mV/amp.

The voltage drop across the lamp filament, $V_L$, is sensed by a voltage sensing circuit 406 that includes a 23.2 kΩ resistor, R1, a 1 kΩ resistor, R2, a 23.2 kΩ resistor, R3, a 1 kΩ resistor, R4, that are connected to pins 1, 2, and 3 of an operational amplifier, OA1, as shown in FIG. 4, while the amplifier is powered by a 6 volt power source. The amplifier can act as a differential amplifier the outputs a voltage proportional to the voltage drop across the filament of the lamp 300. Other electrical components having different electrical properties and functions can also be arranged to form a voltage sensing circuit to sense the voltage drop across the filament, $V_L$.

The voltage across the filament, $V_L$, can be sensed by a four-wire sensing circuit. For example, as shown in FIG. 4, the wires that power the filament 302 are connected to the lamp as are the wires used for sensing the voltage across the filament, which go from resistors R1 and R3 of the voltage sensing circuit to the filament of the lamp. Separating the power wires from the sensing wires is helpful for reducing errors in the measurement of the voltage drop across the filament 302. For example, changes in the resistance of the lamp power wires can be caused by changes in ambient temperature or by Joule heating of the wires. Thus, measuring the voltage drop across a path that includes the power wires measures the voltage drop across the combination of the filament and the power wires. In the four-wire circuit, because only negligible current flows through either of the sense wires, the voltage drop across the filament 302 alone can be measured.

Figure 3B:
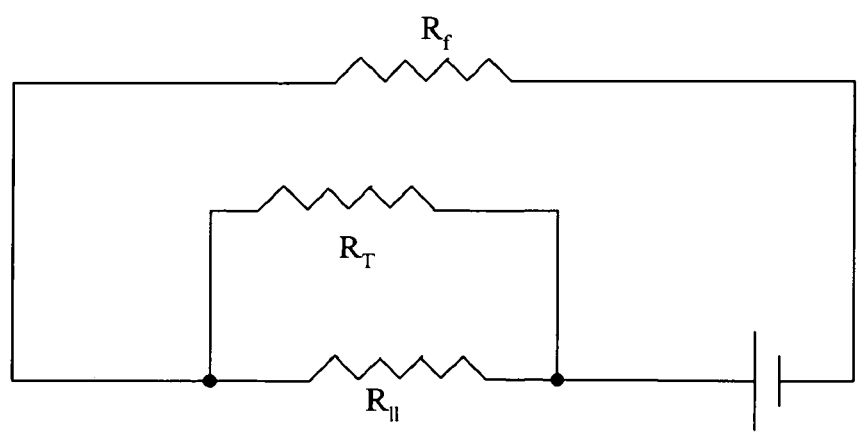
FIG. 3B is a schematic equivalent circuit diagram of the incandescent lamp shown in FIG. 3A.

Nevertheless, even in the four-wire circuit when the sense wires are connected to the base of the bulb of the lamp, the sense wires measure the voltage drop across at least a small portion of the wires that deliver electrical power to the filament. This portion of the power wires is shown as the lamp lead wires 308 in FIG. 3A. Thermally-induced changes in the resistance of the lamp lead wires 308 can be compensated by attaching a negative temperature coefficient thermistor of appropriate value arranged in parallel with the lamp leads. As shown in FIG. 3B, the filament 302 is modeled as a resistor having a resistance equal to $R_f$, and the lamp lead wires 308 are modeled as a resistor having a resistance $R_{ll}$. A thermistor having a temperature-dependent resistance, $R_T$, is connected in parallel across the resistor, $R_{ll}$. Thus, the total equivalent resistance of the lamp, $R_{tot}$, is equal to $R_f$ plus $R_{ll}$ in parallel with $R_T$, (i.e., $R_{tot}=R_f+R_T R_{ll}/(R_T+R_{ll})$). The temperature-dependent resistance characteristics of the thermistor are chosen such that as the resistance of $R_{ll}$ increases with temperature (e.g., from heating by the filament), the resistance of $R_T$ will decrease by an amount that causes the total resistance of $R_f$ and $R_{ll}$ in parallel with $R_T$ to remain constant, to a first-order approximation, thus maintaining a constant filament temperature and light output. The appropriate value of $R_T$ is typically determined empirically to minimize the light output change at lamp turn-on. The arrangement of temperature-dependent resistance of the thermistor in parallel with the lead wires 308 improves short-term and long-term stability of the lamp output.

Referring again to FIG. 4, the gain in the particular embodiment of the voltage-sensing circuit 406 shown in FIG. 4 is about 43 mV/volt. At the desired lamp operating voltage of 5 volts, the voltage-sensing circuit 406 generates 43 mV/V*5 volts or 215 mV. The voltage sense signal, which is output from pin 1 of OA1, and the current sense signal, which is output from wire 408 of voltage divider 404, are input to the operational amplifier, OA2, which compares the voltage sense signal to the current sense signal. The output of the amplifier OA2 is input to a power MOSFET, X1, that regulates the current through the lamp. Other components having different electrical properties and functions can also be chosen to compare the voltage sense signal to the current sense signal. Capacitor C1 compensates for thermal lag in the lamp and causes the circuit to be dynamically stable.

If the filament resistance drops below 5Ω, indicating that the filament temperature is below its desired value, the voltage across the lamp will drop more than the current through the lamp. Thus, the voltage from the voltage sense signal input into OA2 will be lower than the voltage input from the current sense signal on wire 408 into OA2, causing the amplifier output to increase. This increases the gate voltage to X1, turning it on, and increasing the drive voltage to the lamp until the filament resistance increases to the desired 5Ω. The value of the adjustable resistor, R8, can be adjusted to drive the filament to a resistance other than 5Ω. Other components having different electrical properties and functions can also be chosen to control the current through the filament 102 and the resistance of the filament.

A 5.6 V Zener diode, D1, ensures that the lamp circuit starts up when it is first turned on. When the circuit is first powered up, the condition that the voltage across the lamp equal a constant times the current through the lamp is satisfied by both the current and the voltage being zero, so without the Zener diode the feedback circuit would not drive cause current to be supplied to the filament because a stable condition exists when both the current through the filament and the voltage drop across the filament are zero. Zener diode, D1, however, forces some amount of current through the lamp, thus ensuring that the circuit starts up and reaches the desired operating conditions, and the feedback circuit takes control of the voltage drop across the filament.

So that the lamp current, $I_L$, does not rise to too high a value, a transistor, X2, clamps the power MOSFET drive transistor, X1, so that the lamp current cannot exceed a maximum value (e.g., 3 amps).

A slow start network 410 including diodes, D2 and D3, a 470 μF capacitor, C5, and 10 kΩ resistor, R13, provides a low pass filter with a time constant of 470 milliseconds that causes the lamp to turn on gradually. The gradual turn on of the lamp avoids current shocks to the filament 102 and thereby extends the life of the filament.

Other components having different electrical properties and functions can also be chosen to ensure that the lamp circuit starts when first turned on, to limit the current through the filament to a maximum operating current, and to ensure that the current in the filament attains its operating value gradually after being turned on.

Thus, drive circuit 400 calculates the filament resistance by dividing the measured lamp voltage by the measured lamp current. The calculated resistance is compared to a desired value, and the lamp drive voltage is adjusted to drive the filament resistance to the desired value. Although a particular analog circuit has been described, the above-described techniques can be implemented with any analog or digital circuit or processor. Other implementations of a circuit for controlling the filament resistance are also possible. For example, the lamp drive voltage can be adjusted to equal the lamp current multiplied by the desired filament resistance (e.g., $V_L = R_L * I_L$).

This lamp driver circuit results in a light source with significantly improved short-term and long-term stability compared to existing filament lamps light sources. Any of the electrical circuits described herein can be implemented as an analog circuit, a digital circuit, or as a combination of digital and analog circuits.

Fiber Optic Cable System

Light from the light source can be used to analyze the electromagnetic reflectance spectrum of a sample. Light can be ported from the light source to the sample in one leg of a fiber optic cable system to illuminate the sample and to excite the sample optically. Light reflected from the sample can be ported from the sample to a spectrograph that measures the reflectance spectrum. Cross talk between light used to excite the sample and reflected light from the sample is reduced by spatially separating the ends of the optical fibers that shine light onto the sample and the ends of optical fibers that receive reflected light from the sample. A third leg of the fiber optic cable system can port light from the light source to the spectrograph, and can be used to calibrate the reflectance spectrum.

Referring again to FIG. 2, the fiber-optic illumination cable 116a is positioned directly in front of the lamp 104 with the end of the fiber-optic cable 116a being at the focal point of the light emitted from the lamp 104. The cable 116a is inserted into position before system use, and a mechanical click stop ensures that the cable 116a is properly positioned and secured in relation to the lamp 104 and the reflector 220.

A second fiber optic cable 116b is used for directly measuring the lamp spectrum to be used in calculating a real time reference signal. This cable 116b is threaded into a port 214 in the optical bench, e.g., at an angle of 15-35 degrees, 10-60 degrees, or 5-90 degrees with respect to the axis of the focused beam of reflected from the reflector 220. Placing the cable 116b into the port 214 at an angle to the focused beam axis results in a reduced intensity of light entering the cable 116b, compared to if the cable were on axis. The off-axis position of the cable 116b reduces the intensity of the light in the cable 116b that is directed to the spectrograph 114 to prevent saturation of the CCD detector in the spectrograph. The light intensity is further reduced by a neutral density filter 230. The attenuator 230 is positioned in the housing of the connector to the cable 116b in the light path between the lamp 104 and the second fiber optic cable 116b. The attenuator 230 transmits light from the lamp 104 to the cable 116b, but reduces the light intensity entering the cable 116b. Locating the attenuator 230 within the cable connector housing ensures that the attenuator does not collect dust and thereby degrade in its optical performance.

Figure 7A:
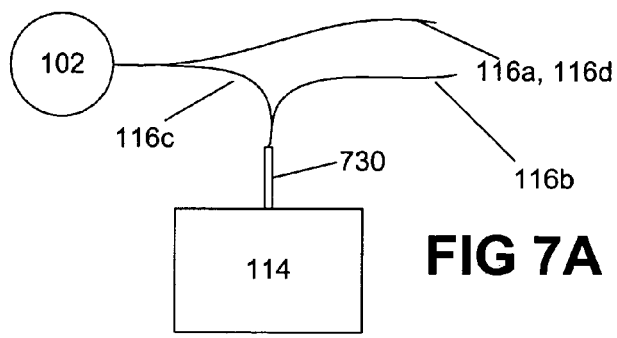
FIG. 7A is schematic diagram of an arrangement of a fiber optic cable for delivering light to a sample, a fiber optic cable for porting reflected light from the sample to a spectrograph, and a fiber optic cable for porting light from a lamp to a spectrograph.

As shown in FIG. 7A, the fiber optic cable can include different fiber bundles 116a, 116c, and 116d. The cable holding the sample bundles 116a or 116d can be contained in a common protective sheath with the cable holding the return bundle 116c outside the unit 100 housing the spectrograph 114 and the light source 104. The sample bundles 116a, 116c, and 116d are gathered together into a single cable before leaving the housing of the system 100, which contains the spectrograph 114 and the lamp 104. The cable containing the bundles 116a, 116c, and 116d connects the spectrograph 114 and the lamp 104 to a probe head 804 that can be located at the sample 102 to perform reflectance measurements on the sample 102.

Figure 7B:
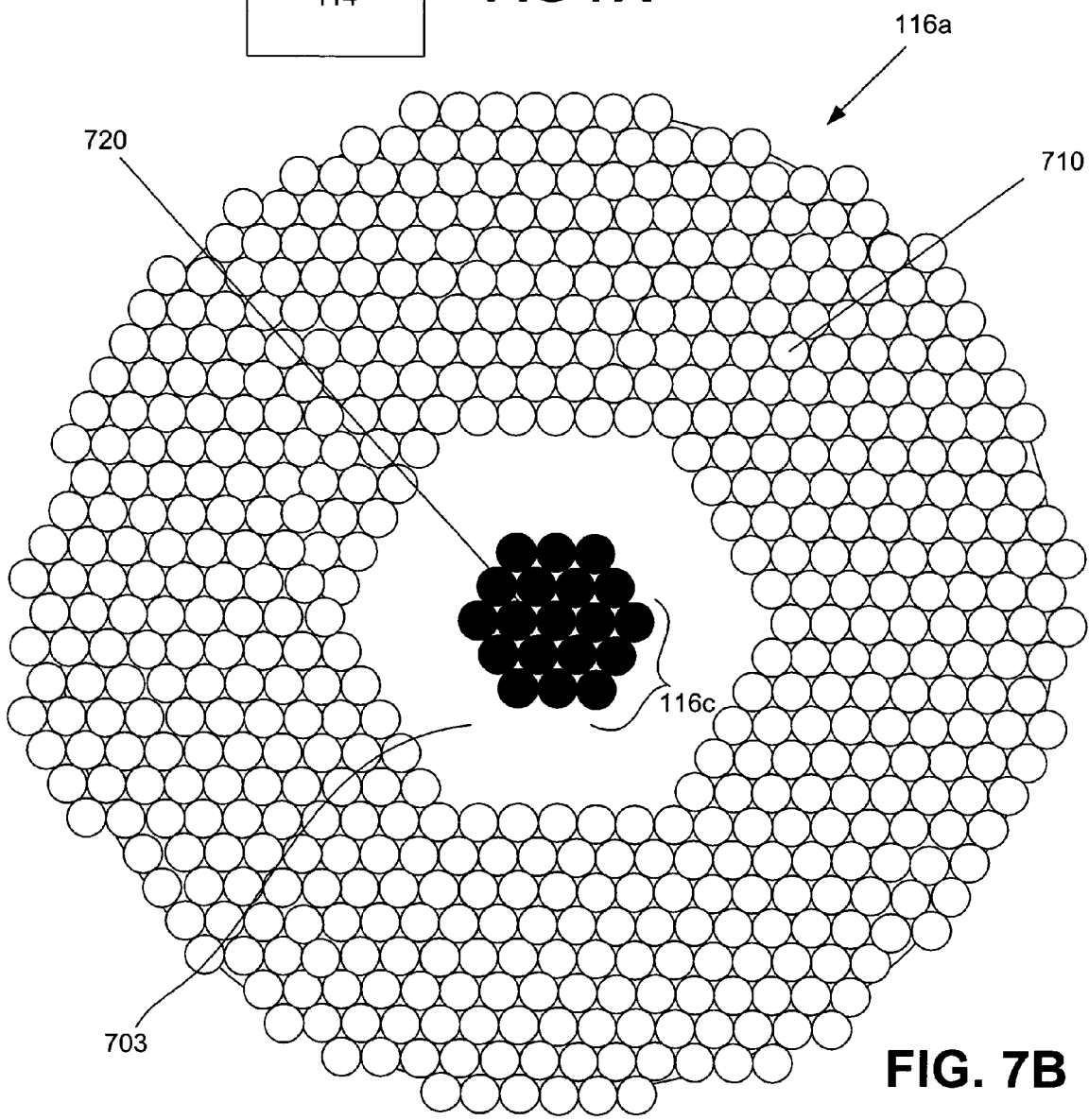
FIG. 7B is a schematic end view of an arrangement of fibers in the fiber optic cable for delivering light to a sample and the fibers in the fiber optic cable for porting reflected light from the sample to a spectrograph.

As shown in FIG. 7B, the sample bundle 116a or 116d can be a ring 710 of individual fibers that surrounds a bundle of fibers 116c formed of individual fibers 720 that return reflected light back to the spectrograph 114. In one embodiment, the outer ring of individual fibers 710 in the sample cable 116a contains approximately 2666, 50 mm glass fibers with a numerical aperture (NA) of 0.66. The central bundle of fibers 720 in the return cable 116c returns reflected light from the sample to the spectrograph 114, and in one embodiment can contain 109, 50 mm glass fibers with an NA of 0.66. In certain embodiments, a gap 703 between the central bundle 720 and outer ring 710 is about 4 mm. Gap 703 can be filled with a solid material (e.g., a metal, such as aluminum, or a plastic, such as polycarbonate) to position and mechanically fix the central bundle 720 with respect to outer ring 710. At the sample end of the fibers, all fibers are oriented perpendicularly to the sample 102. Along the length of the fiber optic cable between the light source 104 and spectrograph 114 at one end and the sample 102 at the other end, the sample bundle 116a that delivers light to the sample is optically shielded with an opaque material, such as black tape, or a sheath of opaque plastic, from the bundle 116c that guides reflected light from the sample to the spectrograph 114, so that any light that might leak out of the bundle 116a is not coupled into the return bundle 116c.

This cable system also contains a third fiber bundle, the reference bundle 116b, which channels an attenuated portion of the lamp light directly to the spectrograph 114. The reference bundle 116b meets the central bundle 116c prior to entering silica rod 740, which feeds into the spectrograph 114, and the diameters of the combined bundle and the rod 740 match the entrance aperture of the spectrograph 114. The reference bundle 116b contains about 13% of the total number of individual fibers in the sample cable 116a and the reference cable 116b. These individual fibers in the reference bundle 116b can also be 50 mm diameter glass fibers with an NA of 0.66.

To improve optical coupling between the lamp 104 and the sample fiber bundle 116a a tapered NA converter can be placed at the end of the sample cable bundle 116a to convert the 0.42 NA of the light source to 0.66 NA of the fibers. This increases the collection efficiency into the fibers by about 15%.

To reduce the NA to 0.22, as required for the spectrograph, a 60 micron fused silica rod 730 can be placed at the end of the fiber bundles 116c and 116b. This silica rod 730 is also used to mix light returned from the sample 102 with light from the reference fibers 116b so the spectrograph grating is uniformly illuminated. To prevent stray light from entering the spectrograph 114, a black, light-absorbing epoxy can be used to surround the silica rod 730.

Figure 8:
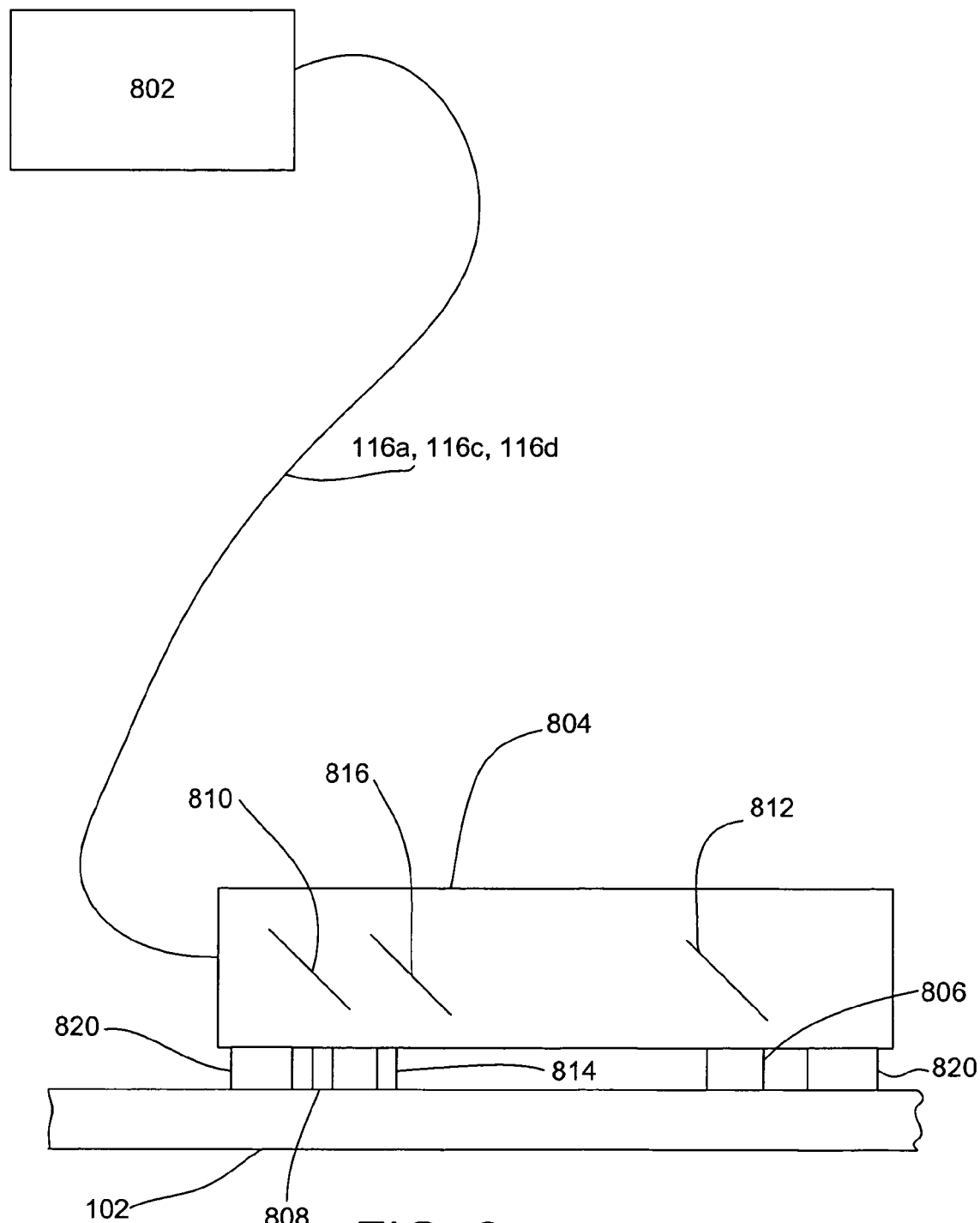
FIG. 8 is a schematic side view of a probe head for delivering light to a sample and for receiving scattered light from the sample.

As shown in FIG. 8, light can be delivered from a unit 802 housing the lamp 104 and the spectrograph 114 to a probe head 804 that delivers light to the sample 102 in a fiber bundle 116a and/or 116d and collects light scattered from the sample and ports the collected light back to the spectrograph 114 in a bundle 116c. The bundles 116a, 116c, and 116d can be contained in a single cable that runs between the housing unit 802 and the probe head 804, and the cable can be several meters long to allow convenient access to and data collection from a sample or a patient. To minimize cross talk between the light illumination bundles 116a and 116d and the light detection bundle 116c, the bundles 116a and 116d delivering illumination light from the lamp 104 to the sample 102 is wrapped in an opaque material, such as black tape, so that any light leaks do not couple into the light return bundle 116c.

In contrast to the implementation described above with reference to FIGS. 7A and 7B, the ends of the optical fibers in the bundle 116c need not be surrounded by the ends of the optical fibers in the bundle 116a, and, as shown in FIG. 8, the probe head 804 can have an illumination light port 806 for delivering light to the sample that is spatially separated from a detection light port 808 for receiving light from the sample. The fiber bundle 116a can be coupled horizontally into the probe head 804, and light from the bundle 116a and then can be reflected from a 45 degree mirror 810 within the probe head and directed vertically towards the sample 102 from the light port 806. Similarly, light scattered from the sample 102 can be collected by the light port 808 and reflected by a mirror 812 into the fiber bundle 116c. Alternatively, the fiber bundles 116a and 116c can enter the probe head 804 horizontally and then bend 90 degrees in a vertical direction such that they are directly coupled to the light ports 806 and 808, respectively.

The illumination light port 806 can contain a 3.5 mm bundle of 50 μm glass fibers having an overall NA of 0.66 for directing light from the housing unit 802 to the sample 102. The detection light port 808 that is coupled to the bundle 116c is spaced a distance (e.g., 30 mm) from the illumination light port 806 and directs diffusely reflected light from the sample to the unit 802 housing the spectrograph 114, where the reflected light can be analyzed. The light port 808 can have a 1 mm diameter detection bundle of 50 μm glass fibers with a collective NA of 0.66.

The probe head 804 can include an additional illumination light port 814 and a mirror 816 configured similarly to the first illumination light port 806 and the mirror 810, but located closer to the detection light port 808 than the first illumination light port 806. For example, the center of the 3.5 mm fiber bundle of the second illumination light port 814 can be located about 2.5 mm from the center of the 1 mm diameter fiber bundle of the detection light port 808, while the 3.5 mm diameter fiber bundle of the first illumination light port 806 can be located about 30 mm from the center of the detection light port 808.

The spacing between the two illumination light ports 806 and 814 and the detection light port 808 can be chosen in conjunction with the intensity and spectrum of the light emitted from the illumination light ports 806 and 814 and the reflectance spectrum of the sample 102 to detect particular desired information about the sample 102. For example, the spectroscopic system 100 can be used to shine near infrared light (e.g., having a wavelength of 700-1000 nm) through a human patient's skin to allow direct, noninvasive measurement of blood chemistry or the chemistry in tissue beneath the skin without removing a blood or tissue sample from the patient. In particular, the system 100 can be used to measure muscle pH, muscle oxygen tension ($PO_2$), and blood hematocrit from continuous wave near infrared spectra obtained with the system.

To record spectral information from a human patient thermally conducting feet 820 (having a size, for example, of about 1×2 cm) of the probe head 804 are placed in contact with a portion of the patient's body, e.g., a portion of the skin, light is shined from one of the illumination ports 806 or 814, and reflected light is collected in the detection port 808. For example, the feet 820 of the probe head 804 can be placed in contact with a patient's forearm, so that light can be emitted from the illumination light ports 806 and 814, reflected off tissue within the patient's body and collected with the detection light port 808. To record information from the patient's muscle, light from one of the illumination light ports 806 and 814 penetrates through the patient's skin and through the fat layer under the skin, which is generally about 3 to 10 mm thick, e.g., 4 or 5 mm thick, to reach the muscle, and then light is scattered from the muscle and collected in the detection light port 808. Using an 8 W lamp 108, about 7 lumens of light can be emitted from a 3.5 mm diameter illumination light port 806 or 814 or about 25 lumens of light can be emitted from a 6 mm diameter illumination light port. It was determined empirically that a spacing of about 30 mm between the illumination light port 806 and the detection light port 808 allowed light collected in the detection light port 808 to include a significant signal from light scattered from muscle tissue underlying the skin and epidermal fat layer. When light is emitted from the second illumination light port 814 that is positioned closer to the detection light port 808 than the first illumination light port 806, the light collected in the detection light port includes a significant signal from light scattered from the overlying skin and epidermal fat layer. This second signal can be used to subtract out a signal component due to scattering from the overlying skin/fat layer in the overall signal recorded when the patient's arm is illuminated with light from the first illumination light port 806. The light emitted from the two illumination light ports 806 and 814 can originate from the same lamp 104, and whether the light is emitted from the first illumination light port 806 or the second illumination light port 814 can be controlled by the shutter 250 (as explained in more detail below).

Two signals, corresponding to a scattering from a shallow skin/fat layer and from a deeper muscle layer can also be obtained by using a single illumination light port and two light detection ports, one of which is located closer to the illumination light port than the other.

The probe head 804 and its feet 820 can be made of a thermally-conductive material (e.g., aluminum or copper) to conduct heat from the light away from the patients skin. If the probe head is made of non-conductive material (e.g., plastic) the heat delivered though the illumination light ports 806 or 814 can be sufficient to dilate blood vessels in the skin and alter skin blood volume of the patient. This effect of heat on skin blood flow can change the spectra recorded from the patient. A thermal conductor in the probe head 804 provides a thermal bridge between the feet 820 at ends of the probe head 804, so that the temperature of the patient's tissue is substantially the same under the illumination ports 806 and detector port 808.

Figure 9A:
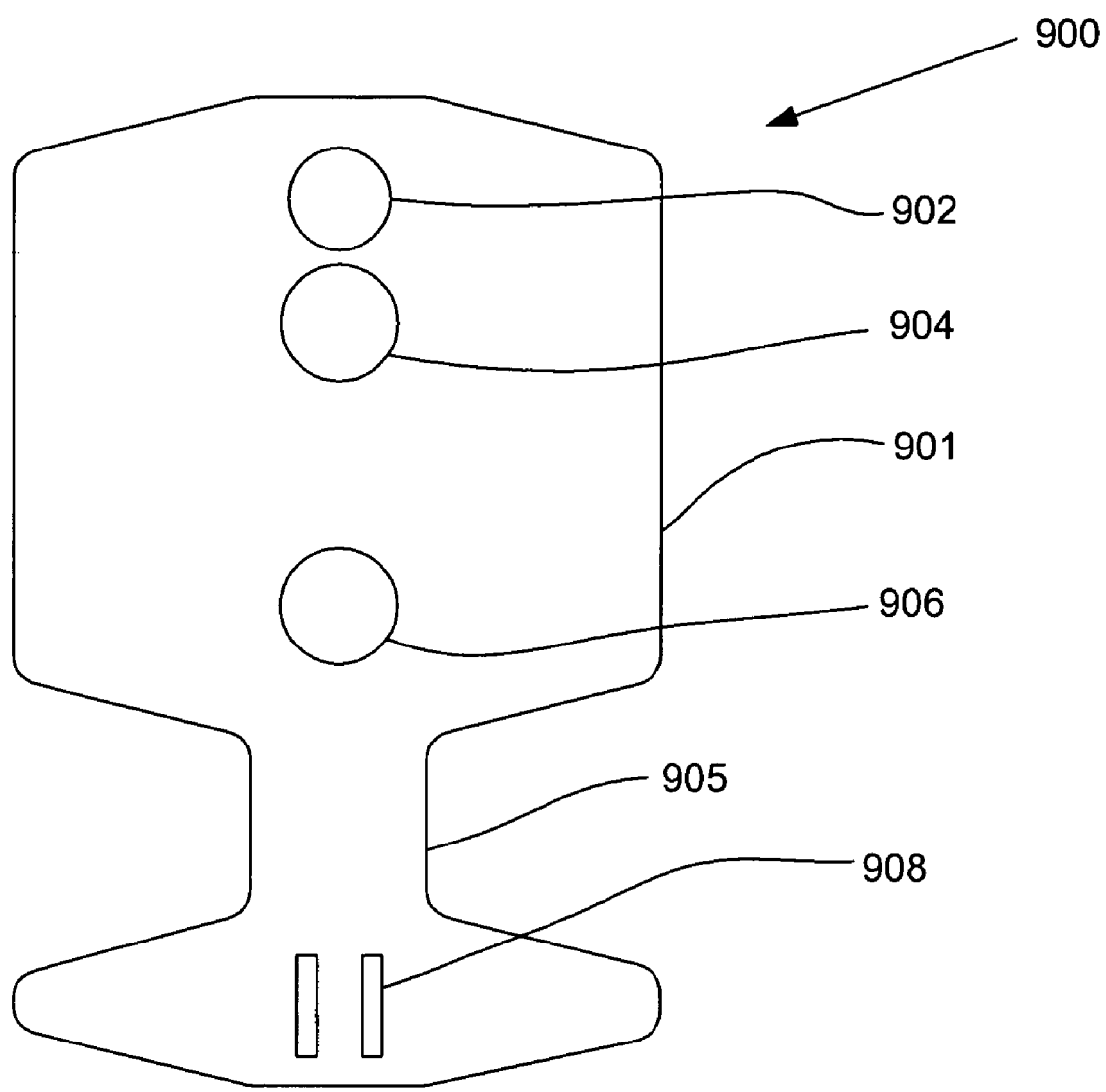
FIG. 9A is schematic top view of a one-piece light shield for holding and shielding the probe head shown in FIG. 8.
Figure 9B:
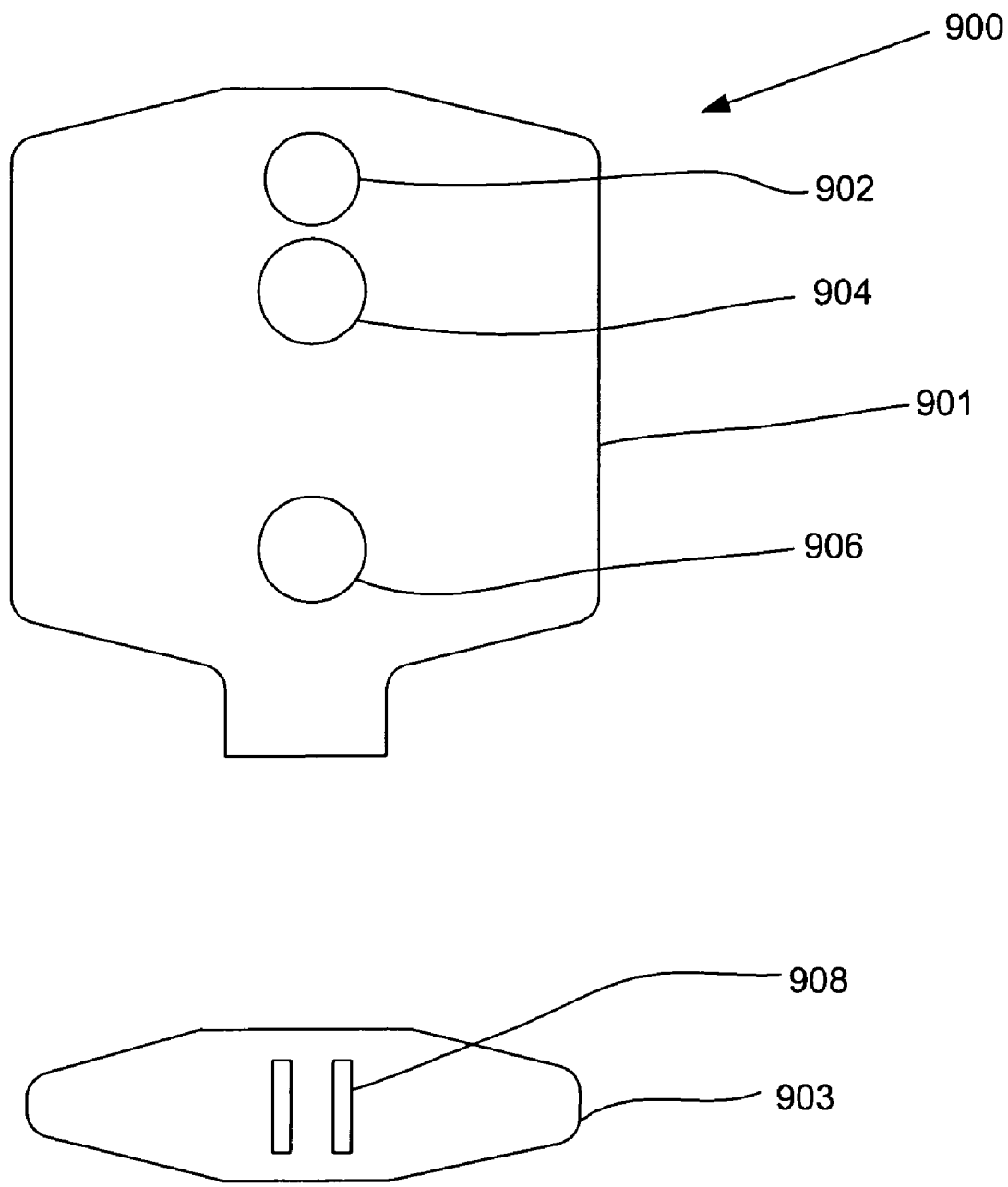
FIG. 9B is schematic top view of a two-piece light shield for holding and shielding the probe head shown in FIG. 8.

Referring to FIGS. 9A and 9B, the probe head 804 can be located in proper position by a light shield 900. The light shield 900 has an opening 902 through which a foot 820 of the probe 400 fits, an opening 904 though which the illumination light ports 806 fits, and an opening 906 through which a second foot 820 fits. The second foot can house the small illumination light port 814 fit and the detection light port 808. Thus, the light shield locates the feet 820 and the illumination and detection light ports 806, 814, and 808 of the probe head 804 in a fixed position. The light shield 900 includes an opaque material that shields the patient's body from stray light, such that only light from the illumination light port 806 or 814 reaches the patient, and such that light collected in the detection light port 808 is due only to light of the known and controlled spectrum that comes from the illumination light port 806. The light shield 900 can extend about 3.5 cm in all directions from the detection light port 808 to shield the detection port from stray light. With the probe head 804 positioned in the light shield 900, the probe head can be positioned against the patient's body, for example by taping, strapping, or sticking the light shield against the patient's body. For example, the probe head 804 can be held against the light shield 900 with double-sided adhesive, which allows the probe head 804 to contact the patient's skin without excessive pressure that could alter the blood volume under the probe head.

As shown in FIG. 9A, the light shield can be made in one piece having a main part 901 that has the various openings or apertures, and a cable management part 903 connected to the main part 901 by a narrow connecting region 905. In another embodiment, FIG. 9B shows a two-piece design in which the cable management part 903 is separate from the main upper part 901. This arrangement enables the two parts to be separated by a distance greater than the length of the connecting region 905. In either embodiment, the light shield cable management part 903 typically includes a clip 908 or other mechanism that can hold a cable that contains the fiber bundles 116a, 116c, and 116d that transport light between the spectrometer unit 802 and the probe head 804. The clip 908 contains the cable, so that the weight of the cable does not torque the probe head from its location on the patient. The shield 900 can be made, e.g., of plastic or other lightweight opaque material. The light shield can also be made of a thermally-conductive material, such as a thin sheet of copper or aluminum to contribute help aid in the radiation of heat, so that the excessive heat is not imparted into the patient's skin.

Optical Bench and Shutter System

An optical bench can include a shutter system 110 for directing the light to different legs of the fiber optic cable system. By controlling the path of the light in the cable system, the shutter system can be used periodically to update the calibration of the spectrometer system used to analyze the reflectance spectrum of the sample 102.

Referring again to FIG. 2, the optical bench 108 provides a mount for a stepper-motor 240 that actuates a new optical shutter 250 of the shutter system 110. The shutter 250 is positioned between the lamp 104 and two fiber optic cables 116a, 116b and is shaped such that it can either block or pass light to each of the fiber optic cables 116a, 116b. Thus, a single spectrograph 114 can measure the spectrum of the sample 102 being tested, the spectrum of the lamp 104 (the "lamp spectrum"), and the "dark spectrum" measured by the spectrograph 114 when no light is fed into the spectrograph. The computer 118 can use the spectrum of the lamp 104 to calibrate the sample spectrum and can use the dark spectrum to subtract background noise from the test spectrum, as explained in further detail below.

Figure 5:
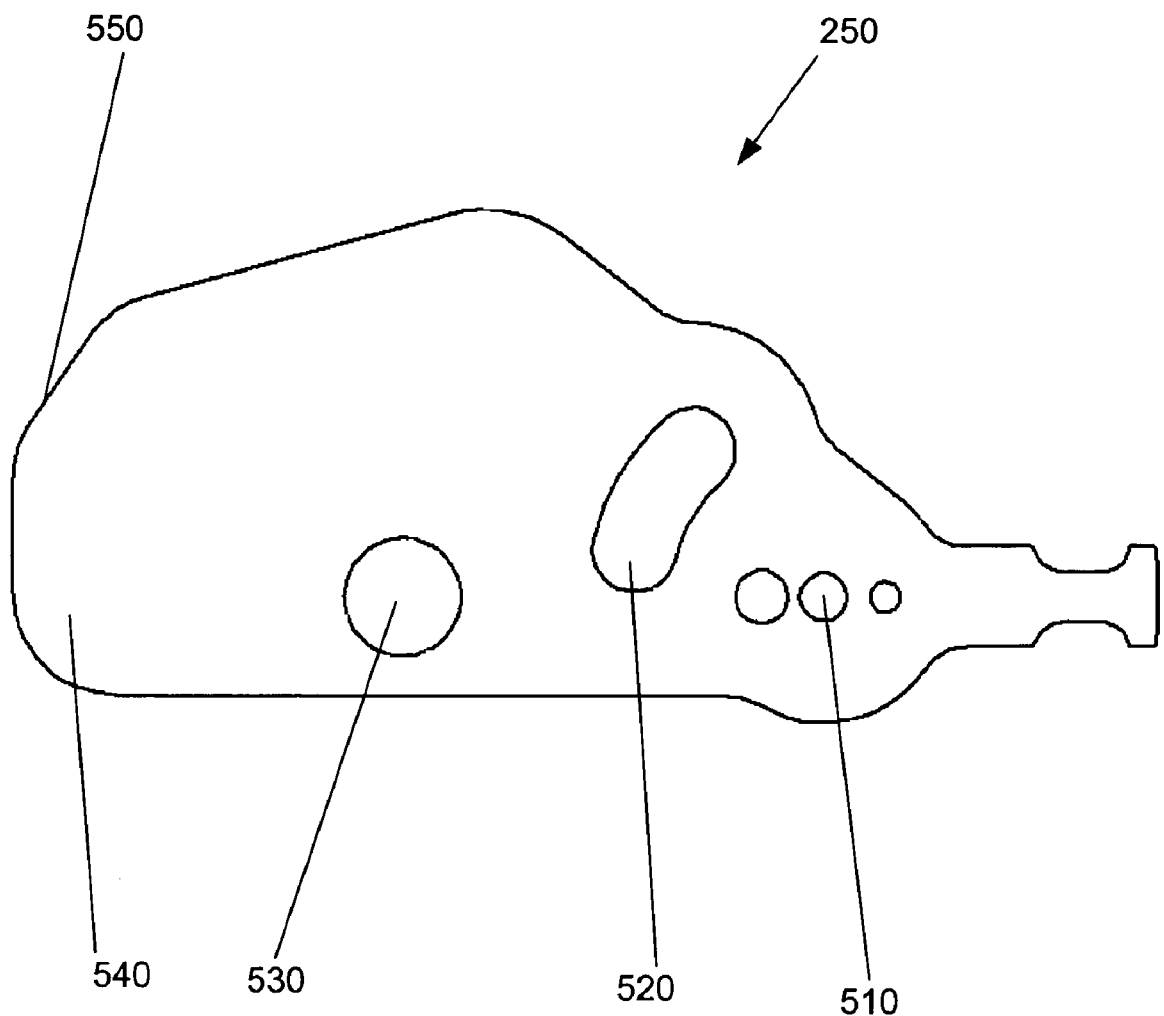
FIG. 5 is a schematic view of a shutter used in the spectrometer system of FIG. 1.

In FIG. 2, only the top edge of the shutter 250 is seen. The profile of the opaque shutter 250 is shown in FIG. 5. The shutter 250 is coupled to the stepper motor 240 by a shaft that passes through a hole 510 in the shutter. When the shaft rotates, the shutter is rotated about an axis passing through the center of the hole 510. A second shaft (not shown) fixed to the optical bench 108 passes through a second hole 520 in the shutter 250 and limits the rotational motion of the shutter 250.

When the shutter 250 is rotated maximally in the clockwise direction, as shown in FIG. 5, a hole 530 in the shutter is located between the lamp 104 and the fiber optic cable 116a that leads to the sample 102, so that light shines through the hole 530 and the sample is illuminated. With the shutter in this position, light reflected from the sample is gathered by cable 116c and guided to the spectrograph 114. In this position the end of the shutter 540 blocks light from entering the reference cable 116b, and the spectrograph 114 measures only the sample channel.

When the shutter 250 is rotated counterclockwise to a middle position, such that the shaft passing through hole 520 is positioned in the middle of the hole 520, hole 530 is rotated out of the beam path of the light emitted from lamp 104 and focused by lens 220. Thus, light does not pass through the hole 530, and is blocked by the opaque shutter 250 from entering the sample cable 116a. Light is also blocked from entering the reference cable 116b by the end of the shutter 540. In this position, the dark current spectrum of the spectrograph (i.e., the dark channel) can be measured.

When the shutter 250 is rotated maximally in the counterclockwise direction, light does not pass through hole 520, and is blocked by the opaque shutter from entering the sample cable 116a. Light passes over the angled edge 550 of the shutter 250 and enters the reference cable 116b and reaches the spectrograph. In this position the spectrograph 114 measures the reference channel.

The measured reflectance spectrum from the sample 102 can be stabilized by real-time calibration of the measured spectrum. The overall approach is to use a temporally updated reference spectrum for the calculation of absorbance. The system 100 allows the collection of an initial 100% reflection reference spectrum to provide an initial calibration of the system 100. Then, continual updating of the reference spectrum is possible using information gathered in real time about changes in the spectrograph (measured by the dark channel) and changes in the lamp output (measured by the reference channel). This corrected reference spectrum is used to calculate absorbance from each sample spectrum acquired, providing a more accurate measurement of sample absorbance.

The computer processes the data in the following manner. To initialize the system, the probe head 804 housing the terminal ends of the fiber optic cables 116a and 116c is positioned over a 100% reflective reference material such as a Spectralon® reflectance standard (available from Labsphere, Inc., North Sutton, N.H.), and a time zero reference spectrum ($R_0(\lambda)$) is recorded from the 100% reflectance standard with the shutter 250 in the sample position while light from the lamp 104 shines through cable 116a and illuminates the 100% reflectance material, and a portion of the reflected light is collected in cable 116c and guided to the spectrograph 114 where the time zero reference spectrum, $R_0(\lambda)$, is recorded. Then, the shutter 250 is moved to the dark position in which it blocks light from entering either illumination fiber 116a or 116d, and the time zero dark spectrum, $D_0(\lambda)$, is recorded. Next, the shutter 250 is moved to allow light to pass into the fiber bundle 116b, such that the time zero lamp spectrum, $L_0(\lambda)$, can be recorded by directing light into the off-axis reference fiber bundle 116b, such that the lamp spectrum can be measured directly. The wavelengths $\lambda$, and the spectra $R_0(\lambda)$, $D_0(\lambda)$, and $L_0(\lambda)$ are recorded in the computer.

To collect data from a sample 102, the probe head 804 is attached to the sample 102 and data collection begins on command. Sample spectra of light reflected from the sample, $S_t(\lambda)$, dark spectra, $D_t(\lambda)$, and lamp spectra, $L_t(\lambda)$, are collected continually at times t>0 until data collection is stopped. Of course, two spectra cannot be collected at exactly identical times. However, an individual spectrum can be collected by the spectrograph in less than a second, so sequential spectra can be collected within seconds or milliseconds of each other. For practical purposes, this is considered simultaneous.

When recording spectra from an object 102, all spectra recorded from the sample 102, $S_t(\lambda)$, and the lamp spectra, $L_t(\lambda)$, can be dark corrected by subtracting the dark spectrum at a time t, $D_t(\lambda)$, from the sample spectrum and the lamp spectrum at the time t. Thus, the dark corrected subject spectrum at a time t is $S_t'(\lambda)=S_t(\lambda)-D_t(\lambda)$ and the dark corrected lamp spectrum at a time t is $L_t'(\lambda)=L_t(\lambda)-D_t(\lambda)$. Initial reference and lamp spectra can also be dark corrected by subtracting the initial dark spectrum and from the initial reference lamp spectra, i.e., $R_0'(\lambda)=R_0(\lambda)-D_0(\lambda)$ and $L_0'(\lambda)=L_0(\lambda)-D_0(\lambda)$.

Next, a reference correction factor, C can be calculated from the dark corrected lamp spectra by dividing the lamp spectrum at a time t by the initial lamp spectrum, i.e., $C_t(\lambda)=L_t'(\lambda)/L_0'(\lambda)$, and a corrected reference spectrum, $R_{ct}$, is calculated by multiplying the reference correction factor by the dark corrected initial reference spectrum, i.e., $R_{ct}(\lambda)=C_t(\lambda)*R_0'(\lambda)$. $R_{ct}(\lambda)$ is written to an array and stored in the computer. Next, the absorbance spectra, $A_t(\lambda)$ is determined by taking the logarithm of the quotient of $R_{ct}(\lambda)$ and the dark corrected sample data, i.e., $A_t(\lambda)=\log(R_{ct}(\lambda)/S_t'(\lambda))$, and written to an array and stored in the computer 118. Thus, after all data are collected and calculations are performed, the computer stores data for $\lambda$, $S_t(\lambda)$, $D_t(\lambda)$, $L_t(\lambda)$, $R_{ct}(\lambda)$, and $A_t(\lambda)$.

In another implementation, if the lamp spectrum is sufficiently stable over time the calibration based on the reference spectrum can be eliminated and the reference cable 116 can be omitted. Then, the optical fiber 116d that leads to the second illumination light port 814 can be positioned such that light from the lamp 104 enters the fiber 116d and the second illumination light port 814 can illuminate the sample 102 when the shutter 250 is rotated maximally in the counterclockwise direction.

In another implementation, an additional hole can be drilled in the shutter 250, and the optical fibers 116a, 116b, and 116d can be positioned such that they can each be illuminated with light from the lamp 104 while the other fibers remain dark. In such a configuration, the system can be calibrated by periodically checking the spectrum of the lamp when the fiber 116b is illuminated, and the spectrum of light scattered by a patient 102 and collected in detection light port 808 can be corrected for surface scattering by the skin/fat layer by alternately illuminating the patient with light provided through fiber 116a and illumination light port 806 and provided through fiber 116d and illumination light port 814.

The shutter can be made from any opaque material. For example, the shutter can be made from a single piece of black anodized aluminum.

A computer 118 sends digital control signals via a parallel (printer) port to the electronics of the shutter driver 112. The control signals specify what position the shutter is in (sample, reference, or dark) and initiates an electronic pulse that causes the shutter to change position. The shutter drive electronics 112 then translates the control signals into appropriate signals to drive the stepper motor 240 that rotates the shutter 250.

Figure 6:
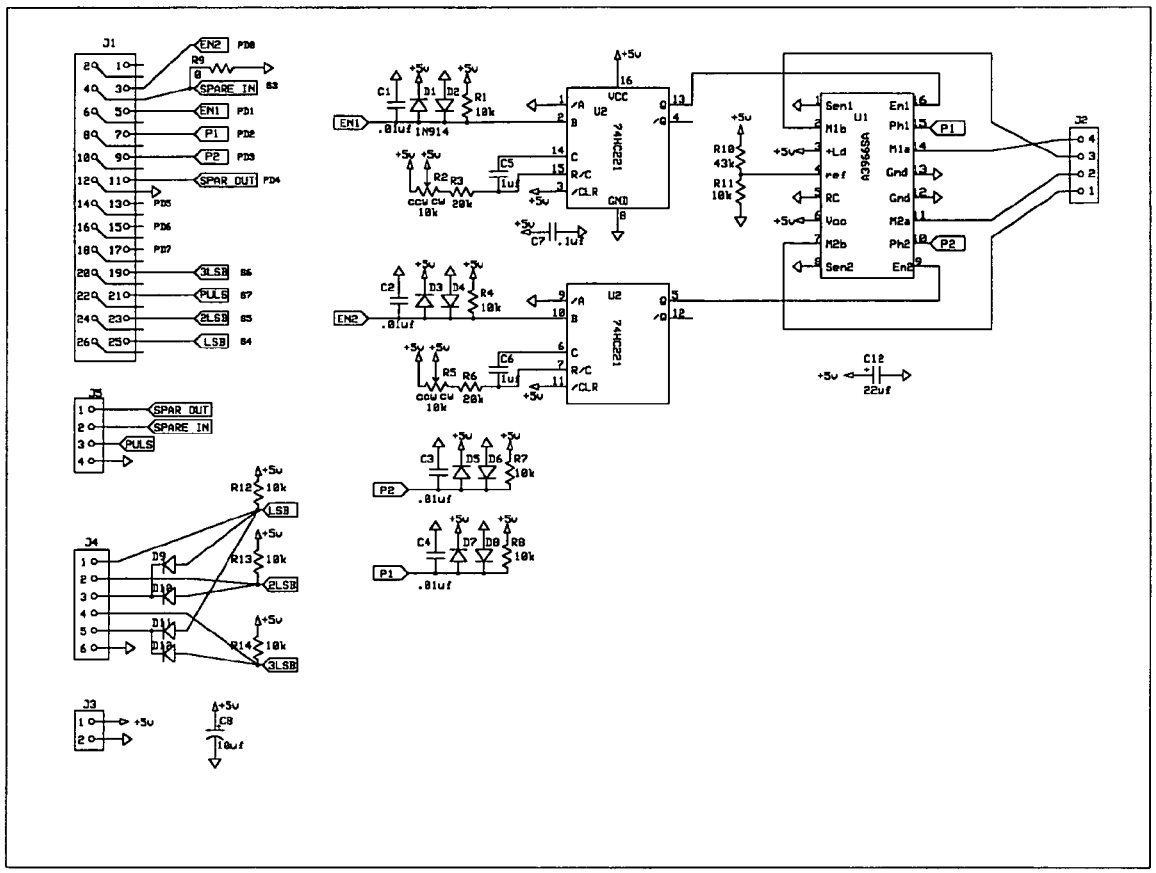
FIG. 6 is a circuit diagram of an electrical circuit for moving the shutter shown in FIG. 5.

The circuitry for controlling the shutter and the front panel buttons is shown in FIG. 6. The parallel port output signals drive the stepper motor 240 via the driver chip U1. Signals P1 and P2 go from the parallel port directly to U1 and thence to the stepper motor 240. Signals EN1 and EN2 are pulses, hence they go to the monostable vibrators at U2 to standardize the pulse width and then to the driver chip and to the stepper motor 240. The drive chip U1 decodes the input signals into positive and negative levels for the stepper motor windings. U1 has sufficient current drive capacity to drive the stepper motor windings directly. Noise suppression networks of reverse bias diodes to ground and +5 volts, capacitor to ground, and pull-up resistor to +5 go on the parallel port signals to the driver.

The five front panel push-button switches go to the diode network of D9, D10, D11, and D12 that encodes them into three bits of data, LSB, 2LSB, and 3LSB, that go to parallel port inputs and thence to the computer 118.

The circuitry for the parallel port is laid out on a custom two-sided printed circuit card for ease of fabrication.

The computer 118 controls the shutter 250 to switch data acquisition in the spectrograph 114 between the sample channel (when light from cable 116c is input to the spectrograph), the reference channel (when light from cable 116b is input to the spectrograph), and the dark channel (when light is blocked from entering both cables 116a and 116b). The computer 118 also controls how the spectrograph 114 collects data. For example, the computer 118 can control the integration time of the spectrograph detector, the number of spectra to be averaged, and the amount of smoothing before spectra are stored in the computer. It is possible for the computer 118 to do this independently for each channel of data acquisition. Parameters are chosen to maximize response in the reference channel and the sample channel without saturating the detector.

Implementation

The equations and algorithms described above can be easily implemented in hardware or software, or a combination of both. The invention can be implemented in computer programs using standard programming techniques following the method steps and figures disclosed herein. The programs should be designed to execute on programmable processors or computers, e.g., microcomputers, each including at least one processor, at least one data storage system (including volatile and non-volatile memory and/or storage elements), at least one input device, such as a keyboard or push button array, and at least one output device, such as a CRT, LCD, or printer. Program code is applied to input data to perform the functions described herein. The output information is applied to one or more output devices such as a printer, or a CRT or other monitor, or a web page on a computer monitor with access to a website, e.g., for remote monitoring.

Each program used in the new system is preferably implemented in a high level procedural or object oriented programming language to communicate with a computer system. However, the programs can be implemented in assembly or machine language, if desired. In any case, the language can be a compiled or interpreted language.

Each such computer program is preferably stored on a storage medium or device (e.g., ROM or magnetic diskette) readable by a general or special purpose programmable computer, for configuring and operating the computer when the storage media or device is read by the computer to perform the procedures described herein. The system can also be considered to be implemented as a computer-readable storage medium, configured with a computer program, where the storage medium so configured causes a computer to operate in a specific and predefined manner to perform the functions described herein.

Although any communications network can be used to obtain results from remote monitoring, the Internet or wireless systems provide useful choices to transmit data.

Uses of the New System

The new system can be used in any field where diffuse reflectance spectroscopy is performed, including, for example, noninvasive medical measurements, chemical and pharmaceutical plant process control, and environmental monitoring. For example, muscle pH, muscle $PO_2$, and blood hematocrit, measures of tissue perfusion in a living patient can be simultaneously and non-invasively determined using near infrared spectroscopy. Because the system is small and portable, it can be used not only in a controlled environment, such as a hospital, but also in the field, such as by paramedics attending to trauma patients. The system is designed to be operational within seconds and provide stable spectra for long term patient monitoring starting from initial treatment of a patient at the trauma site, though evacuation, transport, and hospitalization. The system can be used to monitor data other than information concerning living patients, such as concentrations of air-born, water-born, and solid-born chemicals (e.g., environmental pollution or contaminants). For example, the system can be use to monitor the mineralogy of drill cores from a drilling site and to measure soil carbon content, soil particle size distribution, soil fertility based the chemical composition of the soil. Additionally, pharmaceutical applications of the system include the identification of raw materials and product quality, the measurement of moisture and solvent content in drying or solvent removal processes, the measurement of residual drug carryover in manufacturing facilities, evaluation mixing quality, and real-time monitoring of fermentation processes. The system can also be used, for example, to measure hydrocarbon mixtures, such as fuels or solvent mixtures to estimate the hydrocarbon class composition from various unknown complex mixtures.

EXAMPLES

The present examples are illustrative and not limiting.

Example 1

The stability of the system 100 was evaluated over a three and a half hour period in a hospital operating room where there was a significant temperature fluctuation of about 7.2° C. around the system 100 during the time period. Such a temperature fluctuation can affect the performance of the light source 104 and/or the spectrograph 114.

During the evaluation spectra of a NIST-traceable Dysprosium Oxide ($DyO_2$) reflectance standard (available from Labsphere, Inc., North Sutton, N.H.) were measured. The $DyO_2$ standard has 3 absorption peaks in the near infrared near 760 nm, 800 nm, and 900 nm. This standard should have a constant absorbance as a function of temperature. A fiber optic probe housing the ends of the sample bundle 116a and the return bundle 116c was mounted above the reflectance standard at a height selected to produce an adequate count rate on the spectrograph detector. Spectra from the standard were collected with a 7 msec integration time and 150 were averaged for each one recorded. The lamp spectra were measured using the "lamp channel." Spectra in the channel were collected with an integration time of 100 msec and 5 were averaged. Absorption spectra were calculated using the corrected reference spectrum every 30 seconds. To investigate lamp stability and the effectiveness of the real time correction, the area under the spectral curve for the lamp and the absorption curve for the $DyO_2$ standard were calculated for the spectral region 700-1000 nm. Stability was assessed by calculating the relative standard deviation of the 12 hour test period. Relative standard deviation is the standard deviation of the measurement over the time period, divided by the average measurement over the same time period and is reported as a dimensionless percentage.

Figure 10:
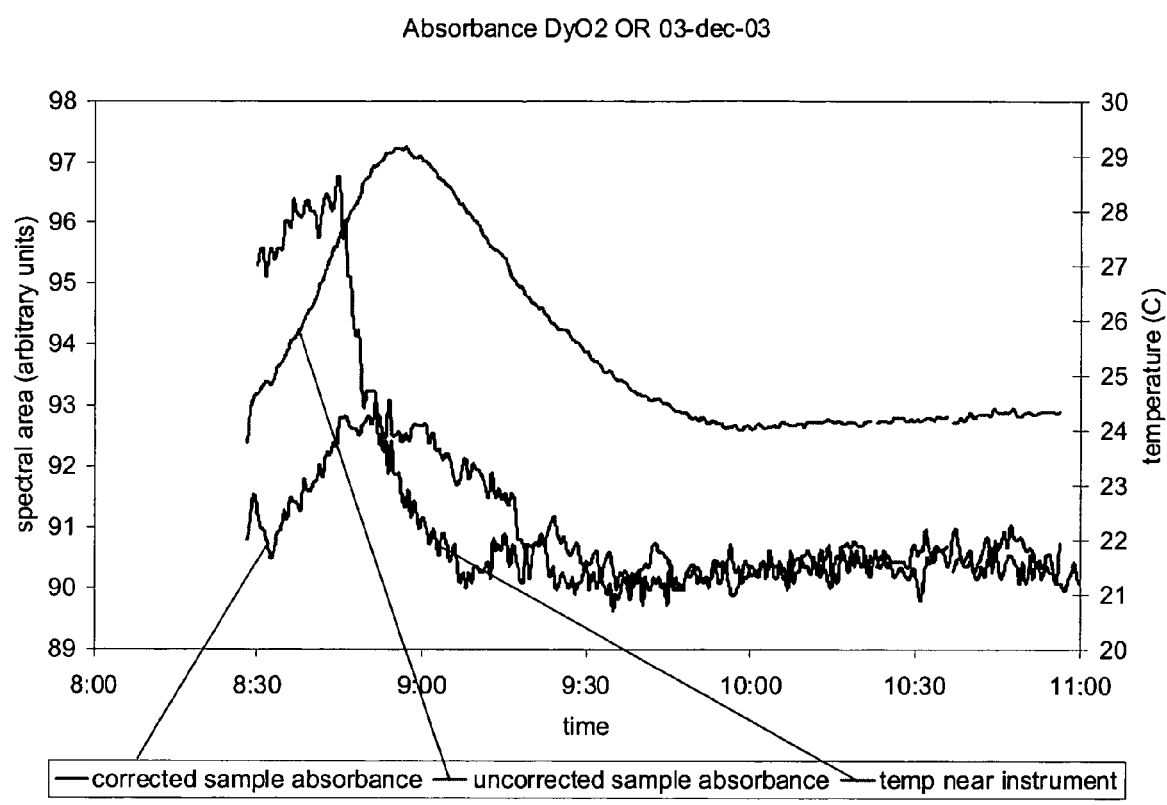
FIG. 10 is a graph of raw and corrected spectra showing the effect of a temperature change on the spectra.

FIG. 10 shows the variation in measured absorbance spectrum of a dysprosium oxide reference standard having absorption bands in the near infrared as a function of a temporal temperature change. Spectra were recorded by the system 100 as a function of time while the temperature changed. Raw, uncorrected spectral area data were are plotted and compared with corrected absorbance data, using the procedures described above. From the data in FIG. 10 it can be seen that the variation with temperature is smaller for the corrected absorbance data (relative standard deviation of 0.9%) than the uncorrected absorbance data (relative standard deviation of 1.6%).

Example 2

In another experiment, pH and Hct values were measured from reflectance spectra of a stable 50% reference target over a period of two hours using the spectrometer system having a stable lamp filament resistance described herein.

Figure 11A:
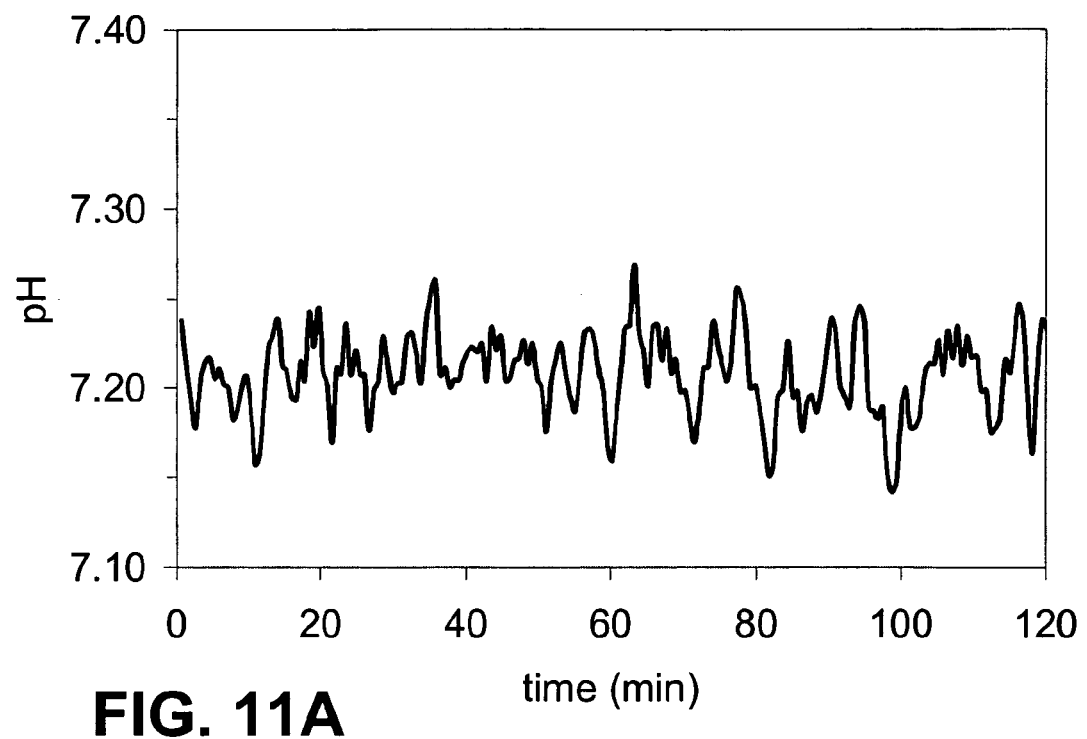
FIGS. 11A and 11B are graphs of muscle pH and hematocrit values obtained from reflectance spectroscopy measurements as a function of time.
Figure 11B:
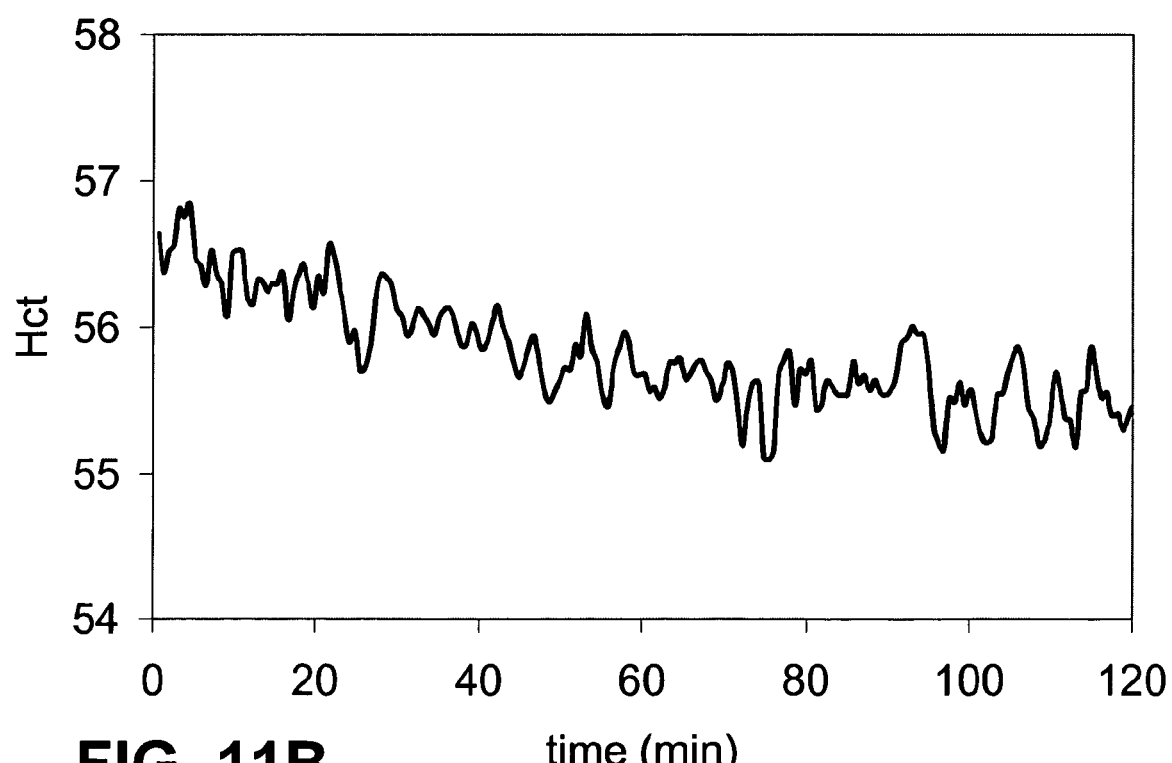
Figure 12A:
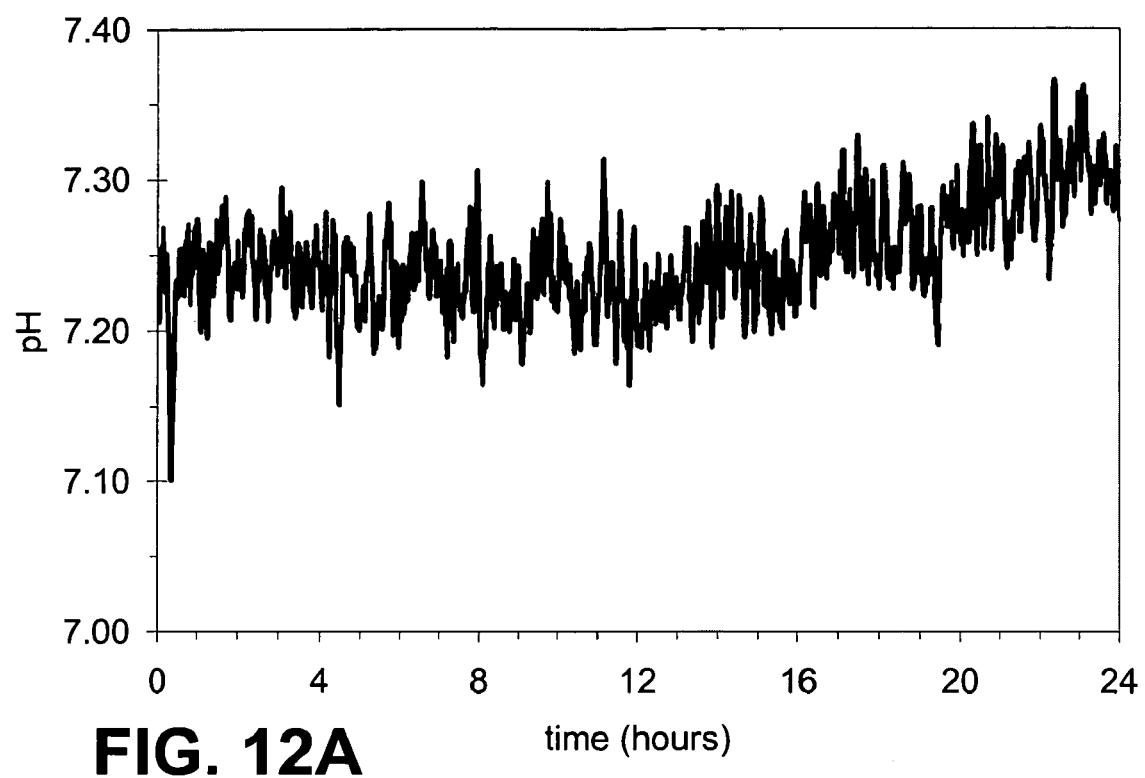
FIGS. 12A and 12B are graphs of muscle pH and hematocrit values obtained from reflectance spectroscopy measurements as a function of time.
Figure 12B:
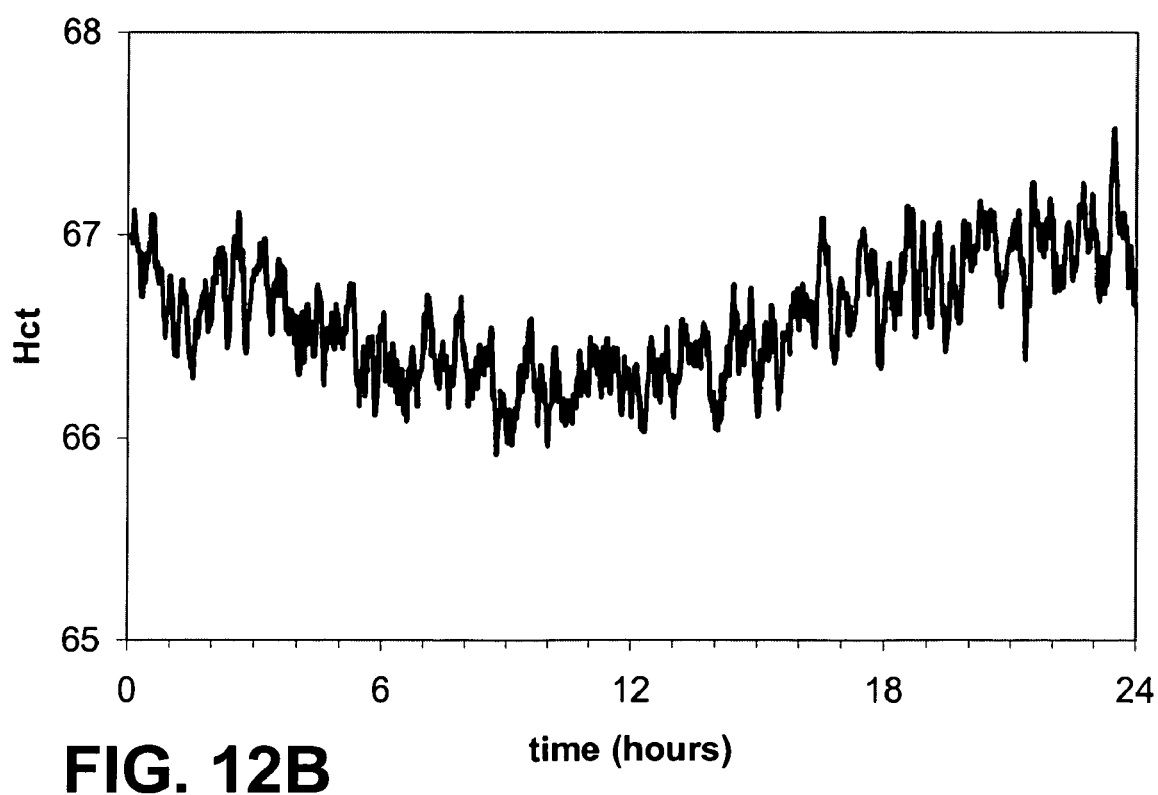

FIGS. 11A and 11B, respectively, show the variation in pH and Hct calculated from the spectra collected from the reference target during the first two hours of a cold lamp start. The standard deviation in the calculated pH data was 0.02 pH units and for the hematocrit, 0.4 Hct units. There was a slight downward trend in the Hct data over the first 30 minutes, corresponding to some uncompensated lamp output, but the calculated error is insignificant in the context of most clinical applications. These data indicate that the lamp driver circuit effectively controls the filament temperature, and no lamp warm up time is required prior to use of the system.

Example 3

In a further experiment, pH and Hct values were measured from reflectance spectra of a stable reference target over a period of 24 hours using the spectrometer system having a stable lamp filament resistance described herein. No effort was made to control the room temperature. The standard deviation in the calculated pH data was 0.04 pH units and the standard deviation in the Hct data was 0.3 Hct units. Some trending upward was observed during the second 12 hours, however the variation of the 24 hour period meets most clinical requirements so there likely would be no need to re-reference the system during the first 12 hours to compensate for temporal drifts in the measurements, and a 24 hour period without collecting a new reference would likely be acceptable.

The data presented in FIGS. 11A, 11B, 12A, and 12B were obtained without using the shutter to compensate for varying lamp intensity, suggesting that the lamp control circuit can be sufficient by itself to ensure long term stability and accurate spectral collection during warm-up.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A spectrometer system comprising:
a thermal light source for illuminating a sample, wherein the thermal light source comprises a filament that emits light when heated;
a spectrograph for measuring a light spectrum from the sample;
an electrical circuit for supplying electrical current to the filament to heat the filament and for controlling a resistance of the filament, the electrical circuit comprising:
a power supply that supplies current to the filament;
first electrical components that sense a current through the filament;
second electrical components that sense a voltage drop across the filament;
third electrical components that compare a ratio of the sensed voltage drop and the sensed current with a predetermined value; and
fourth electrical components that control the current through the filament or the voltage drop across the filament to cause the ratio to equal substantially the predetermined value.

2. The system of claim 1, wherein the first electrical components comprise a sense resistor, wherein a voltage across the sense resistor is proportional to the current through the filament.

3. The system of claim 1, wherein the second electrical components comprise a differential amplifier that generates a signal proportional to a voltage drop across the filament.

4. The system of claim 1, wherein the third electrical components comprise a differential amplifier that compares a signal indicative of a current through the filament with a signal indicative of a voltage drop across the filament.

5. The system of claim 4, further comprising a voltage divider that multiples a ratio between the signal indicative of the current through the filament and the signal indicative of the voltage drop across the filament by a conversion factor.

6. The system of claim 1, wherein the fourth electrical components comprise a transistor adapted for driving the filament with a current to ensure a substantially constant filament temperature.

7. The system of claim 1, further comprising fifth electrical components that gradually ramp up the current supplied to the filament when the power to the filament is turned on.

8. The system of claim 7, wherein the fifth electrical components comprise a low pass filter.

9. The system of claim 7, further comprising sixth electrical components that limit the current supplied to the filament below a maximum value.

10. A method of controlling a spectrum of light emitted from a heated filament, the method comprising:
supplying electrical current from a power supply to heat the filament;
sensing a current flowing through the filament;
sensing a voltage drop across the filament;
comparing a ratio of the sensed voltage drop and the sensed current with a predetermined value; and
controlling the current or the voltage drop to cause the ratio to equal the predetermined value.

11. The method of claim 10, further comprising compensating for a temperature-dependent change in a resistance of electrical connectors that supply current to the filament by introducing an additional temperature-dependent change in an electrical connection between the power supply and the filament.

12. The method of claim 10, further comprising driving the filament with a current controlled to ensure a substantially constant filament temperature.

13. The method of claim 10, further comprising gradually ramping up the current supplied to the filament when the power to the filament is turned on.

14. The method of claim 10, further comprising:
shining the light on a sample;
collecting light scattered from the sample;
analyzing the collected light in a spectrograph to measure properties of the sample; and
outputting one or more of the measured properties from the spectrograph.

15. A spectrometer system comprising:
a light source;
a spectrograph;
an first optical beam path for guiding light from the light source to a sample;
a second optical beam path for guiding light from the light source to the spectrograph;
a third optical beam path for guiding light reflected from the sample to the spectrograph;
a shutter for blocking and unblocking the light in the first beam path from the sample and for blocking and unblocking light in the second beam path from the spectrograph; and
a processor adapted for analyzing light spectra from light guided into the spectrograph and adapted for correcting the spectra for a dark current in the system based on spectra recorded when both the first and second optical beam paths are blocked and adapted for correcting the spectra for temporal changes in the spectrum of the light source based on a plurality of spectra recorded at different times when light is guided into the spectrograph along the second beam path.

16. The spectrometer system of claim 15, wherein the first optical beam path comprises a first optical fiber and the second optical beam path comprises a second optical fiber that is optically shielded from the first optical fiber.

17. The spectrometer system of claim 15, further comprising:

a memory adapted for storing an initial lamp spectrum and a later lamp spectrum recorded from light guided to the spectrograph through the second beam path, wherein the later lamp spectrum is recorded at a time later than the initial lamp spectrum, and adapted for storing an initial reference spectrum recorded from light guided through the first optical beam path to a reference sample, scattered by the reference sample having a known reflectance spectrum, and guided to the spectrograph from the sample through the third optical beam path, and wherein the processor is further adapted for correcting a spectrum of light that has been guided to a test sample from the light source and scattered from the sample to the spectrograph, wherein the correction is based on the initial lamp spectrum, the later lamp spectrum, and the initial reference spectrum.

18. The spectrometer system of claim 15, wherein the light source comprises a filament that emits light when heated, and wherein the spectrometer system further comprises an electrical circuit for supplying electrical current to the filament to heat the filament and for controlling a resistance of the filament, the electrical circuit comprising:

a power supply that supplies current to the filament;

first electrical components that sense a current through the filament;

second electrical components that sense a voltage drop across the filament;

third electrical components that compare a ratio of the sensed voltage drop and the sensed current with a predetermined value; and fourth electrical components that control the current through the filament or the voltage drop across the filament to cause the ratio to equal substantially the predetermined value.

19. The spectrometer system of claim 18, wherein the fourth electrical components are adapted for driving the filament with a current controlled to ensure a substantially constant filament temperature.

20. A method for correcting a spectrum measured by a spectrometer system having a spectrograph and a light source for illuminating a sample with light output from the light source, the method comprising:

recording a reference spectrum, $Ro(\lambda)$, from a reference sample having a known reflectivity spectrum when light from the light source is shined on the reference sample;

recording an initial lamp spectrum, $Lo(\lambda)$, of the light output from the light source at an initial time when light from the light source is shined into the spectrograph;

recording a subsequent lamp spectrum, $Lt(\lambda)$, of the light output from the light source at a time later than the initial time when light from the light source is shined into the spectrograph;

recording a spectrum from a test sample, $S(\lambda)$;

correcting the spectrum from the test sample using data from the reference spectrum, the initial lamp spectrum, and the subsequent lamp spectrum, to produce a corrected spectrum; and outputting the corrected spectrum.

21. The method of claim 20, wherein the reference sample reflects approximately 100% of light directed at the reference sample over a predetermined wavelength range.

22. The method of claim 20, wherein correcting the spectrum includes multiplying the spectrum, $S(\lambda)$, by $Ro(\lambda)* (Lt(\lambda)/Lo(\lambda))$.

23. The method of claim 20, wherein light from the light source is directed toward the reference sample, the test sample, or the spectrograph depending on a position of a shutter that is adapted to selectively block light from reaching the reference sample, the test sample, or the test sample.

24. The method of claim 23, wherein the position of the shutter can be changed by rotating the shutter about an axis.

* * * * *